United States Patent [19]
Dale et al.

[11] Patent Number: 5,856,092
[45] Date of Patent: Jan. 5, 1999

[54] DETECTION OF A NUCLEIC ACID SEQUENCE OR A CHANGE THEREIN

[75] Inventors: James Langham Dale, Moggill; Peter Timms, East Ipswitch; Terence Patrick Walsh, Acacia Ridge, all of Australia

[73] Assignee: Geneco Pty Ltd, Brisbane, Australia

[21] Appl. No.: 429,659

[22] Filed: Apr. 27, 1995

Related U.S. Application Data

[63] Continuation of Ser. No. 205,132, Feb. 28, 1994, abandoned, which is a continuation of Ser. No. 744,766, Aug. 13, 1991, abandoned which is a continuation-in-part of PCT/AU90/00058 Feb. 13, 1990.

[30] Foreign Application Priority Data

Feb. 13, 1989 [AU] Australia .................................. PJ2703
Feb. 13, 1990 [IE] Ireland ...................................... 501/90

[51] Int. Cl.$^6$ ............................. C12Q 1/68; C12P 19/34; C07H 21/00; C12N 15/00
[52] U.S. Cl. ......................... 435/6; 435/91.1; 536/24.33; 536/25.32; 935/76; 935/77
[58] Field of Search ..................... 435/6, 91.1; 536/23.1, 536/24.33, 25.32, 25.4; 935/76, 77; 436/94

[56] References Cited

U.S. PATENT DOCUMENTS

| | | | |
|---|---|---|---|
| 4,307,189 | 12/1981 | Kit ................................................ | 435/6 |
| 4,656,127 | 4/1987 | Mundy ......................................... | 435/6 |
| 4,683,195 | 7/1987 | Mullis et al. ................................ | 435/6 |
| 4,851,331 | 7/1989 | Vary et al. ................................... | 435/6 |
| 4,863,849 | 9/1989 | Melamede ................................... | 435/6 |

FOREIGN PATENT DOCUMENTS

| | | |
|---|---|---|
| A-69724/87 | 9/1987 | Australia . |
| A-70152/87 | 9/1987 | Australia . |
| 62364/86 | 12/1987 | Australia . |
| A-80097/87 | 4/1988 | Australia . |
| 11937/88 | 9/1988 | Australia . |
| A-14005/88 | 10/1988 | Australia . |
| A-21781/88 | 4/1989 | Australia . |
| A-26755/88 | 6/1989 | Australia . |
| 84302648 | 10/1984 | European Pat. Off. . |
| 0297379 | 1/1989 | European Pat. Off. . |
| WO 83/01459 | 4/1983 | WIPO . |
| WO 86/03782 | 7/1986 | WIPO . |
| PCT/US89/00120 | 7/1989 | WIPO . |
| WO 89/10414 | 11/1989 | WIPO . |
| WO 90/01069 | 2/1990 | WIPO . |
| WO 90/06042 | 6/1990 | WIPO . |

OTHER PUBLICATIONS

Mitchell et al., "Affinity Generation of Single Stranded DNA following the Polymerase Chain eaction: Application to Dideoxy Sequencing," Journal of Cellular Biochemistry, Supplement 13E, Abstracts 18th Annual meeting, WH 214, Apr. 1989.
Smith, "DNA Sequence Analysis by Primed Synthesis" in Methods in Enzymology, vol. 65, pp. 560–581 (1980).
Mitchell, et al. Journal of Cellular Biochemistry, Supplemental 13E, 1989, p. 298.
Sommer et al., "Minimal homology requirements for PCR primers", Nucleic Acids Research, vol. 17, No. 16, 1989, p. 6749.
Ballabio et al., Nature, 343, p. 220 (Jan. 18, 1990).
Grimberg et al., Nuc. Acids Res. 17, p. 8390 (1989).
Signer et al., Nuc. Acids Res. 16, p. 7738 (1988).

Primary Examiner—Bradley L. Sisson
Attorney, Agent, or Firm—Marshall, O'Toole, Gerstein, Murray & Borun

[57] ABSTRACT

A method for detecting a specific polynucleotide sequence in a material is disclosed. The method includes exposing said material to an oligonucleotide primer having a sequence complementary to part of said specific polynucleotide sequence wherein said primer binds to part of said polynucleotide sequence when present in said material. Primer bound to the polynucleotide sequence is extended wherein any extended primer includes a detectable element and/or a separation element. Any extended primer is then separated into a fraction wherein said fraction does not have detectable element not included in said extended primer. One then determines whether any extended primer is present in said fraction by assaying said fraction for said extended primer wherein the presence of said extended primer is indicative of the presence of the specific polynucleotide sequence in said material and the absence of said extended primer is indicative of the presence of the specific polynucleotide sequences in said material and the absence of said extended primer in said fraction is indicative of the absence of the specific polynucleotide sequence in said material.

29 Claims, 9 Drawing Sheets

SIZE STANDARDS
(BASES)

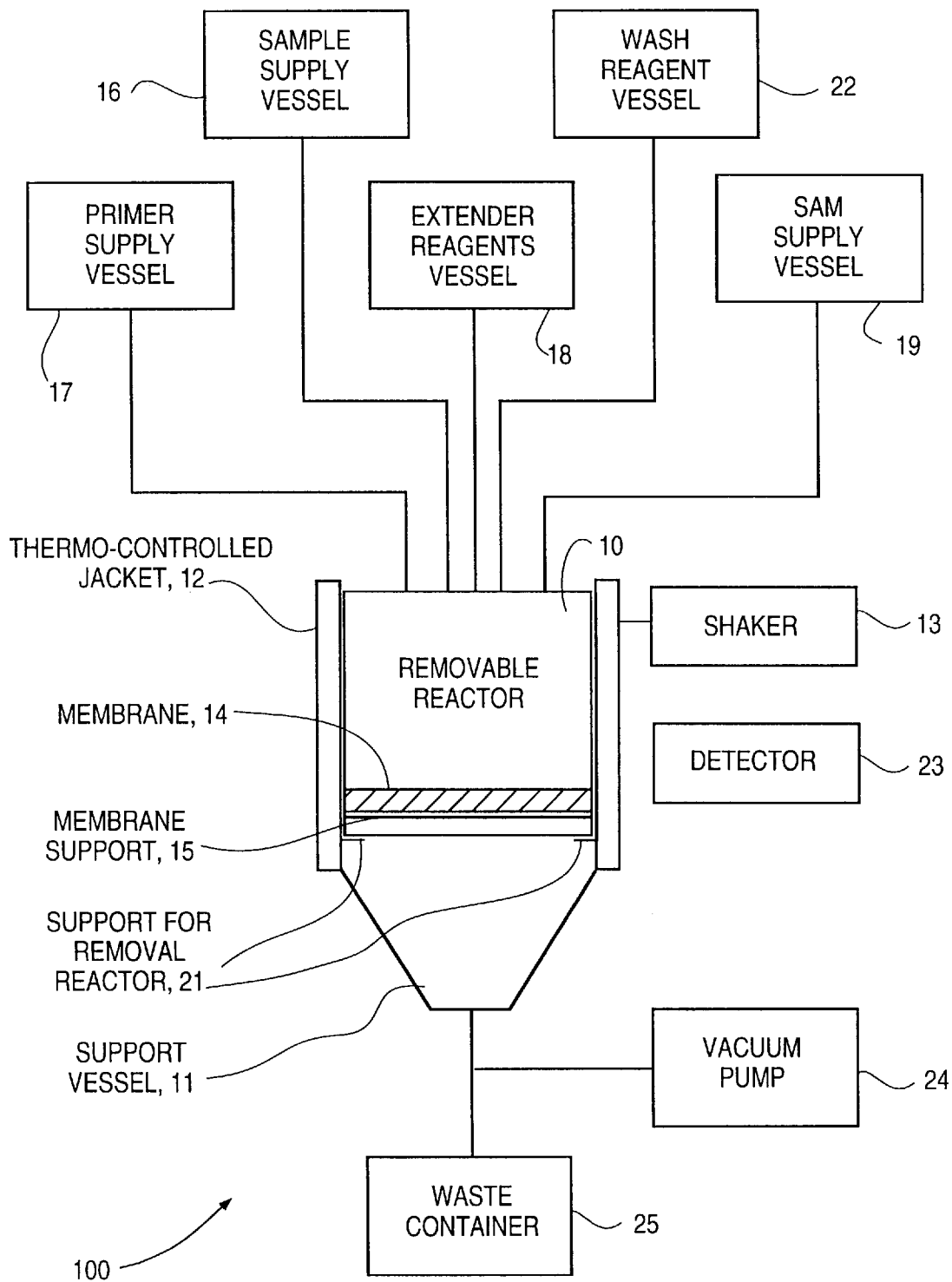

FIG. 5A

PRIOR TO EXTENSION

NORMAL
1613

PCR Primer 1
5' <u>TTTCCTGGATTATGCCTGGCACCATTAAAGAAAATATCAT</u> CTT TGGTGTTTCCTATGATGAATATAGATAC 3'
   AAAGGACCTAATACGGACCGTGGTAATTTCTTTTATAGTA GAA ACCACAAAGGATACTACTTATATCTATG
                                                        <u>PCR Primer 2</u>

Biotinylated Specific Primer (BSP-1)
5' B-TTTCCTGGATTATGCCTGGCACCATTAAAGAAAATATCAT

508 DELETION

1613
PCR Primer 1
5' <u>TTTCCTGGATTATGCCTGGCACCATTAAAGAAAATATCAT</u> TGGTGTTTCCTATGATGAATATAGATAC 3'
   AAAGGACCTAATACGGACCGTGGTAATTTCTTTTATAGTA ACCACAAAGGATACTACTTATATCTATG
                                                   <u>PCR Primer 2</u>

Biotinylated Specific Primer (BSP-1)
5' B-TTTCCTGGATTATGCCTGGCACCATTAAAGAAAATATCAT

FIG. 5B

AFTER EXTENSION

NORMAL

1613
PCR PRIMER 1
5' <u>TTTCCTGGATTATGCCTGGCACCATTAAAGAAAATATCAT</u> CTT TGGTGTTTCCTATGATGAATATAGATAC 3'
AAAGGACCTAATACGGACCGTGGTAATTTCTTTTATAGTA GAA ACCACAAAGGATACTACTTATATCTATG
                                                                                             PCR PRIMER 2

BIOTINYLATED SPECIFIC PRIMER (BSP-1)
5'B-TTTCCTGGATTATGCCTGGCACCATTAAAGAAAATATCAT C$^{358}$

508 DELETION

1613
PCR PRIMER 1
5' <u>TTTCCTGGATTATGCCTGGCACCATTAAAGAAAATATCAT</u> TGGTGTTTCCTATGATGAATATAGATAC 3'
AAAGGACCTAATACGGACCGTGGTAATTTCTTTTATAGTA ACCACAAAGGATACTACTTATATCTATG
                                                                                             PCR PRIMER 2

BIOTINYLATED SPECIFIC PRIMER (BSP-1)
5'B-TTTCCTGGATTATCCCTGGCACCATTAAAGAAAATATCAT T$^{358}$

DETECTION OF A NUCLEIC ACID SEQUENCE OR A CHANGE THEREIN

This application is a continuation of U.S. patent application Ser. No. 08/205,132 filed Feb. 28, 1994, now abandoned, which is a continuation of U.S. patent application Ser. No. 07/744,766, filed on Aug. 13, 1991, now abandoned, which is a continuation-in-part of International Application Number PCT/AU90/00058, filed on Feb. 13, 1990.

TECHNICAL FIELD

This invention relates to a method for detecting a specific polynucleotide sequence in a material, a method for detecting at least two different specific polynucleotide sequences in material having a plurality of different polynucleotide sequences, methods for detecting whether a specific nucleotide or base is at a particular position in a specific polynucleotide sequence, methods for detecting whether the same or different specific nucleotides or bases are at particular positions in at least two different specific polynucleotide sequences in material having a plurality of different polynucleotide sequences, a screening method for detecting the presence of at least two different specific polynucleotide sequences in material having a plurality of different polynucleotide sequences and screening methods for detecting whether the same or different specific nucleotides or bases are at particular positions in at least two different specific polynucleotide sequences in material having a plurality of different polynucleotide sequences.

BACKGROUND ART

At present, the most common technique for the detection of polynucleotide sequences is hybridization using oligonucleotide or polynucleotide probes. For this technique, the target nucleic acid is usually bound, irreversibly, to a solid support such as cellulose or nylon. The labelled probe is then added in solution under hybridizing conditions and if there is sequence homology between the probe and the target nucleic acid, the probe will form a hybrid molecule with the target polynucleotide. This hybrid can be detected in a variety of ways such as by radiolabelling or biotin labelling. The disadvantages of this technique are, firstly, that it requires considerable operator expertise, secondly, the technique is lengthy and time-consuming and thirdly, cannot be easily automated. Often the entire procedure can take more than 48 hours.

The liquid-solid methods normally employed for detecting specific nucleic acids in samples include Southern blot, Northern blot and dot blot hybridizations. These methods are slow, inefficient, technically demanding and are not easily automated. The Southern and Northern blot protocols have the further disadvantage of inefficient transfer of nucleic acid from gel to paper. Other groups have used liquid-solid hybridizations in which a capture probe is bound to a solid support and the DNA sequence of interest in the sample becomes bound to the capture probe. An example of this is in Australian Patent specification no. AU-70152/87 which describes using at least two oligonucleotide probes, which are complementary to mutually exclusive regions of the same target nucleic acid in a liquid hybridization format to anneal the probes to the target, if it is present, and detecting the presence of the target by immobilisation of the two-probe target sandwich by one of the probes and subsequent detection of the other probe. However, this method requires a second, detector probe to hybridise to the DNA sequence of interest. This step reduces the specificity of the assay and subsequently increases background. The present invention overcomes this problem by involving only one probe which acts both as capture probe and as detector probe.

In contrast to liquid-solid hybridization, liquid-liquid hybridization has very rapid kinetics and improved sensitivity due to greater access of the probe to the target sequence. For example, Gene-Probe, Inc., uses a liquid hybridization hydroxapatite method to detect DNA sequences. The main disadvantage of this system is that it relies on adsorptive discrimination of double-stranded DNA from single-stranded DNA sequences rather than sequence-specific separation of hybrid from excess probe. The present invention overcomes these disadvantages by allowing the nucleic acid hybridizations to occur in solution followed by the removal of the "hybrid" molecules onto a solid support matrix. Another potential advantage of liquid hybridization is that a generalised solid support can work for a multitude of targets if the support-binding probes are labelled with the same capture molecule.

Several cases exist (Australian Patent specification nos. AU-A-70152/87, AU-A-26755/88, AU-A-53105/86, AU-B-89575/82 and AU-A-80097/87) which use a combination of two oligonucleotide probes to detect specific nucleic acid sequences in a sample. All these require the use of two short sequences of DNA on the target. These sequences must both be conserved in all possible target, must be mutually exclusive and non-overlapping and must have a similar G+C ratio to enable both probes to hybridize to their complementary sequence under the same conditions.

There is related background art concerning the use of a capture probe to detect the nucleic acid sequence of interest and to remove it from solution by binding the hybrid to a solid support matrix (Australian Patent specification nos. AU-A-70152/87, AU-A-53105/86, AU-A-21781/88, AU-A-69724/87, AU-A-14005/88). However, these techniques use separate capture and detector probes, resulting in a number of disadvantages as detailed above. The present invention overcomes these problems by using a single capture/detector probe system.

There are many examples available of attaching non-radioactive reporter molecules to DNA, to enable the detection of specific hybrids. However, when biotin is incorporated into the DNA molecule for detection, even though several biotin molecules may be incorporated per target molecule (thereby increasing the sensitivity of detection) the mechanism of visualising the incorporated biotin is complex and time consuming.

By contrast, the incorporation of other non-radioactive reporter molecules (such as fluorescent, luminescent, chemiluminescent molecules) enables rapid and simple detection of the target sequence. However, the present art only enables a single reporter molecule to be attached to each target sequence. This fact reduces the overall sensitivity of the final assay. The present invention overcomes both these problems at the one time by using a chemiluminescent detection system for simple, rapid detection and also by incorporating several detector molecules into each target, thereby significantly increasing assay sensitivity.

There is, therefore, a demand for a simple method which utilises the rapid kinetics of liquid hybridization, which only requires a single probe for analysis, and which results in stable hybrids thereby allowing the unhybridized material to be easily removed from the sequences to be detected. Accordingly, the present invention provides a liquid hybridization system in which a single probe hybridizes to the sequence of interest and is then covalently extended to produce a stable hybrid. This hybrid is then captured on to a support matrix and subsequently washed to removed unhybridized material. The system described by the present invention is simple, rapid, sensitive, can be read visually or on a simple plate reader, and may be readily automated.

In this area of nucleic acid hybridization there is a need to detect two broad types of diseases: infectious and genetic. In relation to infectious diseases, a number of DNA based systems have been described to detect diseases caused by bacteria such as Salmonella, Neisseria, parasitic organisms such as Chlamydia and Rickettsiae, viruses such as hepatitis B and protozoa such as Plasmodium. However, all of these suffer one or more of the disadvantages listed above.

In relation to genetic diseases which are characterised by a mutation (deletion, insertion, point mutation or translocation), the technology is less well developed. These types of diseases are currently diagnosed either by using restriction fragment length polymorphism (RFLP) analysis or by precise hybridization of short oligonucleotide probes. RFLP detection requires that a restriction enzyme site is altered by the mutation and this is not always the case. In addition, RFLP analysis requires the use of Southern blot hybridization for detection. The use of short oligonucleotide probes to detect point mutations also has several serious disadvantages. In particular, the hybridization conditions must be precise to ensure that a single base-pair mismatch does not result in hybridization. In practice, salt concentration and temperature determine the specificity of the hybridization conditions and these are not easily controlled to the required preciseness. The present invention overcomes the need for Southern hybridization analysis and for precise control of hybridization conditions. It achieves this by the specific primer probe hybridizing to a constant section of the gene adjacent to the mutation and allowing the enzyme, a DNA polymerase, to extend the DNA chain up to and including the nucleotide or base mutation. By manipulation of the dideoxynucleotide added to the polymerase reaction all of the possible nucleotide changes can be detected.

Detection of both infectious and genetic diseases requires the incorporation of some type of labelled molecule into the system. Various radioactive isotopes or radioactivity labelled compounds may be used as labels. However, radioactive labels have several disadvantages, including; (i) hazardous, (ii) expensive, (iii) limited shelf life, (iv) require expensive equipment for measuring the signal generated. More recently, a range of non-radioactive substances have been used to detect DNA molecules. Examples of non-radioactive labels are fluorescent, luminescent, chemiluminescent, enzymatic or immunological compounds. Labels based on the affinity of biotin and avidin or streptavidin, lanthanide chelates, lectins and proteins may also be used. The preferred detection means would be by spectroscopy or photochemistry or by the formation of a detectable complex between the label moiety and the polypeptide, lectin, or antibody linked to an entity capable of generating a detectable change, including enzymes such as; alkaline phosphatase or horseradish peroxidase.

However, what is lacking in the current technology is a single system which encompasses: (i) a rapid means of detecting a polynucleotide sequence, (ii) which is sufficiently sensitive to detect low numbers of the target sequence in the sample and (iii) which is non-radioactive. At present, no single system satisfies all these requirements.

As a final aspect, the need to detect specific polynucleotide sequences in a sample requires the organisation of all steps either; (i) into a simple kit format, or (ii) into an automated device. Whereas both, kits and automated machines, are available for detecting proteins by way of antibodies, no systems are yet available which simply, rapidly and inexpensively detect specific polynucleotide sequences in a sample.

OBJECTS OF INVENTION

It is an object of this invention to provide a method for detecting a specific polynucleotide sequence in a material.

Another object is to provide a method for detecting at least two different specific polynucleotide sequences in material having a plurality of different polynucleotide sequences.

A further object is to provide methods for detecting whether a specific nucleotide or base is at a particular position in a specific polynucleotide sequence.

Yet another object is to provide methods for detecting whether the same or different specific nucleotides or bases are at particular positions in at least two different specific polynucleotide sequences in material having a plurality of different polynucleotide sequences.

A further object is to provide a screening method for detecting the presence of at least two different specific polynucleotide sequences in material having a plurality of different polynucleotide sequences.

Another object is to provide screening methods for detecting whether the same or different specific nucleotides or bases are at particular positions in at least two different specific polynucleotide sequences in material having a plurality of different polynucleotide sequences.

DISCLOSURE OF INVENTION

The following abbreviations and definitions apply throughout the specification and claims:

SP—specific primer: a nucleotide sequence complementary to a portion of the target sequence Target—the nucleotide sequence to be detected in the sample; can be derived from, for example, any infectious or parasitic organism including any virus, fungus, bacteria, mycoplasma, nematode, protozoan, etc.

Polymerase Enzyme—any DNA dependent DNA polymerase or RNA dependent DNA polymerase dNTP—all four deoxyribonucleotides that is dATP, dCTP, dGTP and dTTP as well as dITP and dUTP ddNTP—all four dideoxyribonucleotides that is ddATP, ddCTP, ddGTP and ddTTP as well as ddITP D—detector molecule: a molecule which can be covalently attached to a nucleotide or nucleotide sequence and that can be subsequently assayed for either directly or indirectly. For example, biotin; radioisotopes of carbon, hydrogen, iodine, phosphorus and sulphur; any antigen; haptens; fluorescent molecules including fluorescein, rhodamine and eosin; enzymes including alkaline phosphates, peroxidases and luciferase; any monoclonal anti body dNTP-D—a detector molecule covalently bound to one of the four deoxyribonucleotides C—capture molecule: a molecule which can be covalently attached to a nucleotide or nucleotide sequence and that will subsequently bind to a specific affinity molecule. For example, biotin (binds with avidin or streptavidin); antibody (binds with antigen); antigen (binds with anti body)

SAM—specific affinity molecule: a molecule that will bind specifically with a particular capture molecule. For example, avidin or streptavidin; an antibody; an antigen SS—solid support: any solid matrix to which the SAM is attached. For example, agarose; polyacrylamide; magnetic beads; polystyrene; microtitre plates; nylon; nitrocellulose Wash—addition and removal of a solution for the purpose of removing unreacted molecules Stringency—conditions of salt and temperature which affect the stability of the hydrogen bonds between two nucleic acid molecules. For example, the hydrogen bonds are most unstable at high stringency reflecting either high temperature or low salt or both.

Assay—any procedure that is specific for detecting the detector molecule and that can be measured either qualitatively or quantitatively X—any one of the four deoxyribonucleotides Y—any one of the four ribonucleotides or deoxyribonucleotides; in the example Y will form hydrogen bonds with X, Ie, a nucleotide sequence of nine Y's will be complementary to a nucleotide sequence of 9 X's Z—any one of the four nucleotides forming a sequence not complementary to the sequence ddT—dideoxythymidine-5'-triphosphate: ddT has been used as example as it base pairs with A in the target sequence.

If the base to be detected was C then ddG would be used, G with ddC and T with ddA.

ddT-C—dideoxythymidine-5'-triphosphate/capture molecule complex: ddT has been used as example as it base pairs with A in the target sequence. If the base to be detected was C then ddG would be used, G with ddC and T with ddA. The capture molecule is covalently attached to ddT and represents any one of the capture molecules described above.

immediately adjacent—means that there are no nucleotides or bases between a primer bound to part of a specific polynucleotide sequence and a specific nucleotide or base to be detected fraction—means at least a portion of a mixture resulting from the reaction of an oligonucleotide primer(s), extending reagents, specific polynucleotide sequence (s), detectable element(s) and/or separation elements intervening sequence—means at least one nucleotide or base between a primer bound to part of a specific polynucleotide sequence and a specific nucleotide or base to be detected oligonucleotide primer—a single stranded nucleic acid molecule with a typical length of 5 to 60 nucleotides but can be 200 or more nucleotides which has a sequence complementary to part of the polynucleotide sequence to be detected specific polynucleotide sequence—a partly or completely known sequence of nucleotides hybridization—the physical association of the oligonucleotide primer with the complementary region of the target polynucleotide sequence to form a double stranded hybrid nucleic acid molecule An interfering detectable and/or separation element is, for instance, one which is the same as that which is incorporated at the position complementary to the specific nucleotide or base to be detected, eg:

(A) Consider a single nucleotide or base $N_1$ to be detected in a specific polynucleotide sequence $S_1$. Assume there is a bound oligonucleotide primer $P_1$ having a sequence complementary to part of $S_1$ and which is bound to $S_1$ Assume there are intervening nucleotides $N_A$, $N_B$ and $N_C$ between $P_1$ and $N_1$. Extend $P_1$ up to and including $N_1$ with complementary nucleotides to $N_A$, $N_B$ $N_C$ and $N_1$, namely, $N_D$, $N_E$, $N_F$ and $N_2$ $S_1$ ($S_1$ corresponding to a separation element) respectively; then the following conditions are required:

$N_A$ $N_B$ or $N_C$ cannot be $N_1$ (B) Consider two nucleotides or bases $N_1$ and $N_2$ to be detected in two different specific polynucleotide sequences $S_1$ and $S_2$. Assume there are two different oligonucleotide primers $P_1$ and $P_2$ (bound to $S_1$ and $S_2$ respectively) having sequence complementary to part of $S_1$ and $S_2$.

Assume there are intervening nucleotides $N_A$, $N_B$ and $N_C$ between $P_1$ and $N_1$ and intervening nucleotides $N_X$, $N_Y$ and $N_Z$ between $P_2$ and $N_2$. Extend (a) $P_1$ up to and including $N_1$ with complementary nucleotides to $N_A$, $N_B$, $N_C$ and $N_1$, namely, $N_D$, $N_E$, $N_F$ and $N_3$-$D_1$ ($D_1$ corresponding to a detectable element) respectively; and (b) $P_2$ up to and including $N_2$ with complementary nucleotides to $N_X$, $N_Y$, $N_Z$ and $N_2$, namely, $N_O$, $N_P$, $N_Q$ and $N_4$-$D_2$ ($D_2$ corresponding to another detectable element); then the following conditions are required:

| | |
|---|---|
| If $N_1 = N_2$ and $D_1 = D_2$ | |
| then $N_A$ ) | |
| $N_B$ ) | |
| $N_C$ ) | cannot be $N_1$ |
| $N_X$ ) | |
| $N_Y$ ) | |
| $N_Z$ ) | |
| If $N_1$ does not equal $N_2$ | $D_1 = D_2$ |
| then $N_A$ ) | |
| $N_B$ ) | |
| $N_C$ ) | cannot be $N_1$ or $N_2$ |
| $N_X$ ) | |
| $N_Y$ ) | |
| $N_Z$ ) | |
| If $N_1$ does not equal $N_2$ | $D_1$ does not equal $D_2$ |
| $N_A$ ) | |
| $N_B$ ) | cannot be $N_1$ |
| $N_C$ ) | |
| $N_X$ ) | |
| $N_Y$ ) | cannot be $N_2$ |
| $N_2$ ) | |

According to a first embodiment of this invention there is provided a method for detecting a specific polynucleotide sequence in a material comprising:

a) exposing said material to an oligonucleotide primer having a sequence complementary to part of said specific polynucleotide sequence wherein said primer binds to part of said polynucleotide sequence when present in said material;

b) extending primer bound to the polynucleotide sequence wherein any extended primer includes a detectable element and/or a separation element;

c) separating any extended primer into a fraction wherein said fraction does not have detectable element not included in said extended primer; and d) determining whether any extended primer is present in said fraction by assaying said fraction for said extended primer wherein the presence of said extended primer is indicative of the presence of the specific polynucleotide sequence in said material and the absence of said extended primer in said fraction is indicative of the absence of the specific polynucleotide sequence in said material.

According to a second embodiment of this invention there is provided a method for detecting at least two different specific polynucleotide sequences in material having a plurality of different polynucleotide sequences comprising:

a) exposing said material to at least two different oligonucleotide primers, wherein each of said different oligonucleotide primers has a sequence complementary to part of one of said different specific polynucleotide sequences and wherein each of said primers binds to part of one of said different specific polynucleotide sequences when present in said material each of said oligonucleotide primers binding to part of a different specific polynucleotide sequence to the other of said oligonucleotide primer(s);

b) extending said different oligonucleotide primers bound to their different specific polynucleotide sequences wherein any extended primer includes a detectable element and/or a separation element;

c) separating any extended primers into at least one fraction wherein said fraction(s) does not have detectable element not included in said extended primer(s); and d) determining whether any extended primers are present in said fraction(s) by assaying said fraction(s) for at least one of said extended primers wherein the presence of said extended primer(s) is indicative of the presence of at least one of the different specific polynucleotide sequences in said material and the absence of said extended primer(s) in said fraction(s) is indicative of the absence of at least one different specific polynucleotide sequence in said material.

According to a third embodiment of this invention there is provided a method for detecting whether a specific nucleotide or base is at a particular position in a specific polynucleotide sequence in material comprising:

a) exposing said material to an oligonucleotide primer having a sequence complementary to part of the specific polynucleotide sequence wherein said primer binds to part of said specific polynucleotide sequence in said material immediately adjacent to the particular position;

b) extending primer bound to the specific polynucleotide sequence with the proviso that the bound primer is only extended up to and including said specific nucleotide or base when said specific nucleotide or base is at the particular position in the specific polynucleotide sequence wherein the extended primer has a detectable element and/or a separation element at a position complementary to said specific nucleotide or base;

c) separating any extended primer into a fraction wherein said fraction does not have detectable element not included in said extended primer; and d) determining whether any extended primer is present in said fraction by assaying said fraction for said extended primer wherein the presence of said extended primer indicates that the specific nucleotide or base is at the particular position in the specific polynucleotide sequence and the absence of said extended primer indicates that the specific nucleotide or base is not at the particular position in the specific polynucleotide sequence.

According to a fourth embodiment of this invention there is provided a method for detecting whether the same or different specific nucleotides or bases are at particular positions in at least two different specific polynucleotide sequences in material having a plurality of different polynucleotide sequences comprising:

a) exposing said material to at least two different oligonucleotide primers, wherein each of said different oligonucleotide primers has a sequence complementary to part of one of said different specific polynucleotide sequences and wherein each of said primers binds to its complementary polynucleotide sequence when present in said material each of said oligonucleotide primers binding to part of a different specific polynucleotide sequence to that of the other primer(s) and wherein each of said primers binds to its complementary specific polynucleotide sequence in said material immediately adjacent to the particular position;

b) extending said different oligonucleotide primers bound to their complementary polynucleotide sequences with the proviso that each of the bound primers is only extended up to and including the particular position when said specific nucleotide or base is at the particular position in the specific nucleotide sequence wherein each of said extended primers has a detectable element and/or a separation element at a position complementary to said specific nucleotide or base;

c) separating any extended primer(s) which has extended only up to a specific nucleotide or base at a particular position into at least one fraction wherein said fraction does not have detectable element not included in said extended primer; and d) determining whether at least one extended primer is present in said fraction(s) by assaying said fraction(s) for said extended primer(s) wherein the presence of an extended primer indicates that a specific nucleotide or base is at a particular position in a specific polynucleotide sequence and the absence of said extended primer (s) in a fraction(s) indicates that at least one specific nucleotide or base is not at a particular position in at least one different specific polynucleotide sequence.

According to a fifth embodiment of this invention there is provided a method for detecting whether a specific nucleotide or base is at a particular position in a specific polynucleotide sequence in material comprising:

a) exposing said material to an oligonucleotide primer having a sequence complementary to part of the specific polynucleotide sequence wherein said primer binds to part of said specific polynucleotide sequence in said material not immediately adjacent to the particular position whereby there is an intervening sequence between the particular position and primer bound to the specific polynucleotide sequence;

b) extending bound primer with the proviso that the bound primer is only extended up to and including said specific nucleotide or base when said specific nucleotide or base is at the particular position in the specific polynucleotide sequence wherein the extended primer has a detectable element and/or a separation element at a position complementary to said specific nucleotide or base with the proviso that the intervening sequence cannot be one where bases or nucleotides complementary to the intervening sequence and which are incorporated into the extended primer cause Incorporation of an interfering detectable and/or separation element;

c) separating any extended primer which has extended only up to a specific nucleotide or base at a particular position into a fraction wherein said fraction does not have detectable element not included in said extended primer; and d) determining whether any extended primer is present in said fraction by assaying said fraction for said extended primer wherein the presence of said extended primer indicates that the specific nucleotide or base is at the particular position in the specific polynucleotide sequence and the absence of said extended primer indicates that the specific nucleotide or base is not at the particular position in the specific polynucleotide sequence.

According to a sixth embodiment of this invention there is provided a method for detecting whether the same or different specific nucleotides or bases are at particular positions in at least two different specific polynucleotide sequences in material having a plurality of different polynucleotide sequences comprising:

a) exposing said material to at least two different oligonucleotide primers, wherein each of said different oligonucleotide primers has a sequence complementary to part of one of said different specific polynucleotide sequences and wherein each of said primers binds to its complementary polynucleotide sequence not immediately adjacent to the particular position whereby there is an intervening sequence between the particular position and primer bound to the specific polynucleotide sequence when present in said material each of said oligonucleotide primers binding to part of a different specific polynucleotide sequence to that of the other primer(s);

b) extending said different oligonucleotide primers bound to their complementary polynucleotide sequences wherein each of the bound primers is only extended up to and including the particular position when said specific nucleotide or base is at the particular position in the specific nucleotide sequence wherein each of said extended primers has a detectable element and/or a separation element at a position complementary to said specific nucleotide or base with the proviso that the intervening sequences cannot be ones where bases or nucleotides complementary to the intervening sequences and which are incorporated into the extended primer(s) cause incorporation of interfering detectable and/or separation element(s);

c) separating any extended primer which has extended only up to a specific nucleotide or base at a particular position into at least one fraction wherein said fraction (s) does not have detectable element not included in said extended primers; and d) determining whether any extended primers are present in said fraction(s) by assaying said fraction(s) for said extended primer(s) wherein the presence of an extended primer(s) indicates that at least one specific nucleotide or base is at a particular position in a specific polynucleotide sequence and the absence of said extended primer(s) in a fraction indicates that at least one specific nucleotide or base is not at a particular position in at least one different specific polynucleotide sequence.

According to a seventh embodiment of this invention there is provided a kit for detecting a specific polynucleotide sequence in a material comprising:

a) an oligonucleotide primer having a sequence complementary to part of said specific polynucleotide sequence;

b) polymerase enzyme for extended the oligonucleotide primer;

c) at least one nucleotide selected from the group consisting of dATP, dCTP, dGTP, dTTP, dUTP, dITP, ddATP, ddCTP, ddGTP, ddITP and ddTTP; and d) a detectable element and/or separation element which is optionally attached to the oligonucleotide primer or one or more of the nucleotides.

According to an eighth embodiment of this invention there is provided a kit for detecting at least two different specific polynucleotide sequences in a material having a plurality of different polynucleotide sequences comprising:

a) at least two different oligonucleotide primers, wherein each of said primers has a sequence complementary to part of one of said specific polynucleotide sequences;

b) polymerase enzyme(s) for extending the different oligonucleotide primers;

c) at least one nucleotide selected from the group consisting of dATP, dCTP, dGTP, dTTP, dUTP, dITP, ddATP, ddCTP, ddGTP, ddITP and ddTTP; and d) a detectable element and/or separation element which is optionally attached to the oligonucleotide primers or one or more of the nucleotides.

According to a ninth embodiment of this invention there is provided a kit for detecting whether a specific nucleotide or base is at a particular position in a specific polynucleotide sequence in a material comprising:

a) an oligonucleotide primer having a sequence complementary to part of the specific polynucleotide sequence wherein said primer binds to part of said specific polynucleotide sequence immediately adjacent to the particular position;

b) a polymerase enzyme for extended the oligonucleotide primer;

c) one nucleotide selected from the group consisting of dATP, dCTP, dGTP, dTTP, dUTP, dITP, ddITP, ddATP, ddCTP, ddGTP and ddTTP with the proviso that said nucleotide is selected whereby bound primer is only extended up to and including said specific nucleotide or base when said specific nucleotide or base is at the particular position in the specific polynucleotide sequence; and d) a detectable element and/or separation element whereby extended primer has a detectable element and/or a separation element at a position complementary to said specific nucleotide or base and a detectable and/or separation element optionally attached to the oligonucleotide primer.

According to a tenth embodiment of this invention there is provided a kit for detecting whether the same or different specific nucleotides or bases are at particular positions in at least two different specific polynucleotide sequences in material having a plurality of different polynucleotide sequences comprising:

a) at least two different oligonucleotide primers, wherein each of said primers has a sequence complementary to part of one of said specific polynucleotide sequences and wherein each of said primers binds to its complementary polynucleotide sequence when present in said material each of said oligonucleotide primers binding to part of a different specific polynucleotide sequence to that of the other primer(s) and wherein each of said primers binds to its complementary specific polynucleotide sequence in said material immediately adjacent to the particular position;

b) a polymerase enzyme(s) for extending the different oligonucleotide primers;

c) at least one nucleotide selected from the group consisting of dATP, dCTP, dGTP, dTTP, dUTP, dITP, ddITP, ddATP, ddCTP, ddGTP and ddTTP with the proviso that said nucleotide is selected whereby bound primer is only extended up to and including said specific nucleotide or base when said specific nucleotide or base is at the particular position in the specific polynucleotide sequence; and d) at least one detectable element and/or separation element whereby each extended primer has a detectable element and/or a separation element at a position complementary to said specific nucleotide or base and a detectable and/or separation element optionally attached to the oligonucleotide primer.

According to an eleventh embodiment of this invention there is provided a kit for detecting whether a specific nucleotide or base is at a particular position in a specific polynucleotide sequence in a material comprising:

a) an oligonucleotide primer having a sequence complementary to part of the specific polynucleotide sequence wherein said primer binds to part of said specific polynucleotide sequence not immediately adjacent to the particular position whereby there is an intervening sequence between the particular position and primer bound to the specific polynucleotide sequence;

b) a polymerase enzyme for extended the oligonucleotide primer;

c) one nucleotide selected from the group consisting of dATP, dCTP, dGTP, dTTP, dUTP, dITP, ddITP, ddATP, ddCTP, ddGTP and ddTTP with the provision that said nucleotide is selected whereby bound primer is only extended up to and including said specific nucleotide or base when said specific nucleotide or base is at the particular position in the specific polynucleotide sequence with the proviso that the intervening sequence cannot be one where bases or nucleotides complementary to the intervening sequence and which are incorporated into the extended primer cause incorporation of an interfering detectable and/or separation element; and d) a detectable element and/or separation element whereby extended primer has a detectable element and/or a separation element at a position complementary to said specific nucleotide or base and a detectable and/or separation element optionally attached to the oligonucleotide primer.

According to a twelfth embodiment of this invention there is provided a kit for detecting whether the same or different specific nucleotides or bases are at particular positions in at least two different specific polynucleotide sequences in material having a plurality of different polynucleotide sequences comprising:

a) at least two different oligonucleotide primers, wherein each of said primers has a sequence complementary to part of one of said specific polynucleotide sequences and wherein each of said primers binds to its complementary polynucleotide sequence when present in said material each of said oligonucleotide primers binding to part of a different specific polynucleotide sequence to that of the other primer(s) and wherein each of said primers binds to its complementary specific polynucleotide sequence in said material not immediately adjacent to the particular position whereby there is an intervening sequence between the particular position and primer bound to the specific polynucleotide sequence;

b) a polymerase enzyme(s) for extending the different oligonucleotide primers;

c) at least one nucleotide selected from the group consisting of dATP, dCTP, dGTP, dTTP, dUTP, dITP, ddITP, ddATP, ddCTP, ddGTP and ddTTP with the proviso that said nucleotide is selected whereby bound primer is only extended up to and including said specific nucleotide or base when said specific nucleotide or base is at the particular position in the specific polynucleotide sequence with the proviso that the intervening sequences cannot be ones where bases or nucleotides complementary to the intervening sequences and which are incorporated into the extended primer(s) cause incorporation of an interfering detectable and/or separation element(s); and d) at least one detectable element and/or separation element whereby each extended primer has a detectable element and/or a separation element at a position complementary to said specific nucleotide or base and a detectable and/or separation element optionally attached to the oligonucleotide primer.

According to a thirteenth embodiment of this invention there is provided an apparatus for performing the method of any one of the embodiments of the invention comprising: a reactor;

means for adding oligonucleotide primer and reagents for extending said primer to said reactor, said means for adding being operatively associated with the reactor;

means for separating extended primer into at least one fraction(s) and for holding said fraction(s), said means for separating being operatively associated with the reactor; and a detector for detecting the presence of any extended primer(s) in said fraction(s), said detector being operatively associated with said means for separating.

According to a fourteenth embodiment of this invention there is provided a screening method for detecting the presence of at least two different specific polynucleotide sequences in material having a plurality of different polynucleotide sequences comprising:

a) exposing said material to at least two different oligonucleotide primers, wherein each of said different oligonucleotide primers has a sequence complementary to part of one of said different specific polynucleotide sequences and wherein each of said primers binds to part of one of said different specific polynucleotide sequences when present in said material each of said oligonucleotide primers binding to part of a different specific polynucleotide sequence to the other of said oligonucleotide primer(s);

b) extending said different oligonucleotide primers bound to their different specific polynucleotide sequences wherein any extended primer includes a detectable element and/or a separation element;

c) separating any extended primers into a fraction wherein said fraction does not have detectable element not included in said extended primer(s); and d) determining whether any extended primers are present in said fraction by assaying said fraction for all of said extended primers wherein the presence of any one of said extended primers is indicative of the present of at least one of the different specific polynucleotide sequences in said material and the absence of all of said extended primer(s) in said fraction is indicative of the absence of all of the different specific polynucleotide sequences in said material.

According to a fifteenth embodiment of this invention there is provided a screening method for detecting whether the same or different specific nucleotides or bases are at particular positions in at least two different specific polynucleotide sequences in material having a plurality of different polynucleotide sequences comprising:

a) exposing said material to at least two different oligonucleotide primers, wherein each of said different oligonucleotide primers has a sequence complementary to part of one of said different specific polynucleotide sequences and wherein each of said primers binds to its complementary polynucleotide sequence when present in said material each of said oligonucleotide primers binding to part of a different specific polynucleotide sequence to that of the other primer(s) and wherein each of said primers binds to Its complementary specific polynucleotide sequence in said material immediately adjacent to the particular position;

b) extending said different oligonucleotide primers bound to their complementary polynucleotide sequences with the proviso that each of the bound primers is only extended up to and including the particular position when said specific nucleotide or base is at the particular position in the specific nucleotide sequence wherein each of said extended primers has a detectable element and/or a separation element at a position complementary to said specific nucleotide or base;

c) separating any extended primer(s) which has extended only up to a specific nucleotide or base at a particular position into a fraction wherein said fraction does not have detectable element not included in said extended primer; and d) determining whether at least one extended primer is present in said fraction by assaying said fraction for all of said extended primers wherein the present of an extended primer indicates that at least one specific nucleotide or base is at a particular position in a specific polynucleotide sequence and the absence of all said extended primers in said fraction indicates that at least one specific nucleotide or base is not at a particular position in any of the different specific polynucleotide sequences.

According to a sixteenth embodiment of this invention there is provided a screening method for detecting whether the same or different specific nucleotides or bases are at particular positions in at least two different specific polynucleotide sequences in material having a plurality of different polynucleotide sequences comprising:

a) exposing said material to at least two different oligonucleotide primers, wherein of said different oligonucleotide primers has a sequence complementary to part of one of said different specific polynucleotide sequences and wherein each of said primers binds to its complementary polynucleotide sequence not immediately adjacent to the particular position whereby there is an intervening sequence between the particular position and primer bound to the specific polynucleotide sequence when present in said material each of said oligonucleotide primers binding to part of a different specific polynucleotide sequence to that of the other primer(s);

b) extending said different oligonucleotide primers bound to their complementary polynucleotide sequences wherein each of the bound primers is only extended up to and including the particular position when said specific nucleotide or base is at the particular position in the specific nucleotide sequence wherein each of said extended primers has a detectable element and/or a separation element at a position complementary to said specific nucleotide or base with the proviso that the intervening sequences cannot be ones where bases or nucleotides complementary to the intervening sequences and which are incorporated into the extended primer(s) cause incorporation of interfering detectable and/or separation element(s);

c) separating any extended primer which has extended only up to a specific nucleotide or base at a particular position into a fraction wherein said fraction does not have detectable element not included in said extended primers; and d) determining whether any extended primers are present in said fraction by assaying said fraction for all of said extended primers wherein the presence of an extended primer indicates that at least one specific nucleotide or base is at a particular position in a specific polynucleotide sequence and the absence of any extended primer indicates that a specific nucleotide or base is not at a particular position in any of the different specific polynucleotide sequences.

Generally the method for the detection of a nucleotide sequence or nucleotide change in a nucleotide sequence uses:

a nucleic acid primer specific to part of a partly or wholly known nucleotide sequence to be detected or specific to part of a partly or wholly known nucleotide sequence which is immediately adjacent to the nucleotide or base change to be detected or specific to part of a partly or wholly known nucleotide sequence which is not immediately adjacent to the nucleotide or base change to be detected but has an intervening sequence between the bound primer and the nucleotide or base change to be detected extension of the primer catalysed by a nucleic acid polymerase enzyme either (i) the attachment of a capture molecule at the 5' end of the specific primer, addition of the target sequence under hybridization conditions and the incorporation of a detector molecule (s) in the enzyme catalysed extended primer or (ii) the attachment of a detector molecule at the 5' end of the specific primer, addition of the target sequence under hybridization conditions and the incorporation of a capture molecule(s) in the enzyme catalysed extended primer capture of the extended primer using a specific affinity molecule attached to a solid support assay for the detector molecule Advantageously, for the first, second, seventh and eighth embodiments extending the primer comprises using at least one nucleotide selected from the group consisting of dATP, dCTP, dGTP, dTTP, dUTP, dITP, ddATP, ddCTP, ddGTP, ddITP and ddTTP. Typically two to four different nucleotides, and especially four different nucleotides are used.

Generally, for the third, fifth, ninth and eleventh embodiments extending the primer comprises using one nucleotide selected from the group consisting of dATP, dCTP, dGTP, dTTP, dUTP, dITP, ddATP, ddCTP, ddGTP, ddITP and ddTTP. Typically one nucleotide selected from the group consisting of ddATP, ddCTP, ddGTP, ddITP and ddTTP is used.

Typically, for the fourth, sixth, tenth and twelfth embodiments extending the primer comprises using at least one nucleotide selected from the group consisting of dATP, dCTP, dGTP, dTTP, dUTP, dITP, ddATP, ddCTP, ddGTP, ddITP and ddTTP. Generally at least one nucleotide selected from the group consisting of ddATP, ddCTP, ddGTP, ddITP and ddTTP is used.

In addition to a nucleotide(s) also typically used in extending the primer are at least one appropriate polymerase enzyme and appropriate buffering agent.

Examples of polymerase enzymes are E.coli DNA polymerase, E.coli DNA polymerase (Klenow fragment), Bacteriophage T7 DNA polymerase, Bacteriophage T4 DNA polymerase, Taq DNA polymerase and AMV Reverse transcriptase.

Buffering agents which buffer aqueous solutions between pH 6–8.5 are generally suitable for use with a polymerase enzyme to extend the primer. Generally a magnesium salt (eg $MgCl_2$ or $MgSO_4$) is included with the buffering agent. A total salt concentration between 50 and 300 mM is generally acceptable.

Temperature of the extending reaction is chosen according to the polymerase enzyme used and is typically in the range 25°–80° C., more typically 30°–70° C.

It is preferred that at least one of the nucleotides has the detectable element.

Alternatively, or in addition, the detectable element is linked to the oligonucleotide primer.

Typically, the detectable element is a radioactive label selected from the group consisting of $^3H$, $^{125}I$, $^{131}I$, $^{14}C$, $^{35}S$ and $^{32}P$ The detectable element may be non-radioactive and generally is selected from the group consisting of an enzymatic group, an immunological group, and a spectroscopically detectable group. The spectroscopically detectable group may be a luminescent group, a chemiluminescent group, an NMR detectable group, a fluorescent group or an 1R detectable group.

Advantageously, the extended primer includes a separation element which facilitates the separation of the extended primer into the first fraction.

Generally, the specific polynucleotide sequence is a DNA sequence or an RNA sequence.

The specific polynucleotide sequence may be from an infectious or disease causing organism which may be live or non-viable viral, bacterial, fungal or Protozoan.

The extending may include:
  adding a plurality of nucleotide types to said primer bound to the polynucleotide sequence to extend said primer; or
  adding a single nucleotide type to said primer bound to the polynucleotide sequence to extend said primer (third, fifth, ninth and eleventh embodiments); or
  adding at least one single nucleotide type to said primer bound to the polynucleotide sequence to extend said primer.

In one particular method of the invention the exposure and primer extension steps occur before the separation step.

In one form of this invention, the separation element is linked to the oligonucleotide primer. Alternatively, the extended primer includes a separation element which facilitates separation of extended primer from the mixture into the first fraction and wherein at least one of said nucleotides has the separation element.

In one form of the invention, the separation step comprises:
  contacting any extended primer with a molecule having affinity for the separation element, the molecule being linked to a support that facilitates the separating; and separating the contacted extended primer(s) to provide the fraction.

Advantageously, the separation element and the molecule are selected from the group listed immediately below:

| Separation Element | Molecule Having Affinity for Separation Element |
|---|---|
| (a) a ligand for which there is a receptor; | a receptor for the ligand; |
| (b) a receptor; | the ligand for the receptor; |
| (c) an antigen; | an antibody for the antigen; |
| (d) an antibody for an antigen; | the antigen; |
| (e) an antiidiotypic antibody; | an antibody for the antiidiotypic antibody; |
| (f) an antibody for an antiidiotypic antibody; | an antiidiotypic antibody for the antibody; |
| (g) a haptenic group; | an antibody for the haptenic group; |
| (h) an antibody for a haptenic group; | the haptenic group; |
| (i) an enzyme; | a binding inhibitor for the enzyme; and |
| (j) a binding inhibitor for an enzyme; | the enzyme. |

Typically, the separation element and the molecule are selected from the group listed below:

| Separation Element | Molecule Having Affinity for Separation Element |
|---|---|
| (a) a ligand for which there is a specific receptor; | a specific receptor for the ligand; |
| (b) a specific receptor; | the ligand for the specific receptor; |
| (c) an antigen; | a specific antibody for the antigen; |
| (d) a specific antibody for an antigen; | the antigen; |
| (e) an antiidiotypic antibody; | an antibody specific for the antiidiotypic antibody; |
| (f) an antibody for an antiidiotypic antibody; | an antiidiotypic antibody specific for the antibody; |
| (g) a haptenic group; | a specific antibody for the haptenic group; |
| (h) a specific antibody for a haptenic group; | the haptenic group; |
| (i) an enzyme; | a tight binding inhibitor for the enzyme; |
| (j) a tight binding inhibitor for an enzyme; | and the enzyme. |

Typical examples of ligands for which there are available receptors are:
  a vitamin such as biotin, a sugar molecule such as glucose or mannose, a hormone such as adrenalin or cortisone and a steroid such as progesterone or testosterone. There are numerous types of ligand which have available receptors and the preceding list is given by way of exemplification only.

The separation typically includes a solid support which is typically selected from the group consisting of latex, magnetic beads, nitrocellulose, agarose, cellulose, polyacrylamide, nylon, glass and polystyrene.

ADVANTAGES

1. General Advantages

A particular advantage of the method of the invention is that the system combines separation and detection elements on the one oligonucleotide after primer extension. Most other systems require the use of a capture probe and a detector probe.

A further advantage is that the system depends on the enzyme driven extension of the primer to incorporate a separation or detection element or elements (depending on configuration) and the the element or elements are therefore covalently attached to the specific primer. Because of this covalent attachment, washing steps can be performed at very high stringency which results in reduced background and increased specificity.

Another advantage is that the method of the invention can be easily automated.

In the method of the invention the steps can be incorporated into a simple kit format.

A further advantage is that an oligonucleotide primer having a sequence complimentary to a conserved or variable region of the genome of the organism of interest can be used and thus can be designed for high or low specificity (i.e., genus specific, species specific or strain specific). a rapid and sensitive method for the detection of specific polynucleotide. sequences or nucleotide changes in specific polynucleotide sequences using a single oligonucleotide probe.

Generally in the method of the invention the detectable hybrid is captured by a solid matrix to allow washing away of unincorporated detectable element. While this is not a difficult step it does add to the time required for processing. The step can be overcome by choosing a detectable element whereby any unincorporated detectable element can be simple inactivated and left in the reaction mix, rather than having to be physically removed.

Generally, a detection sensitivity in the order of $10^3$–$10^4$ genome copies is quite adequate for detecting a wide range of virus, bacterial and parasitic organisms which are usually present in moderate to high numbers in their respective disease states. For defect diseases in which the infectious agent Is present only in very low numbers (e.g. HIV) the method of the invention can make use of the technique of polymerisation chain reaction (PCR) which is effectively an amplification step which results in an increase in sensitivity.

2. Infectious Disease Diagnosis Advantages

The method of the invention permits the rapid, simple and non-hazardous detection of specific polynucleotide sequences in samples of biological material especially infectious agents. The detectable sequence may be part of an infectious organism such as a virus, bacterium, Protozoan or fungus, or part of a gene in which an abnormality results in a genetic disorder: for example, sickle-cell anemia, cystic fibrosis, α-thalassemia or β-thalassemia.

Non-viable organisms can be detected using the method of the invention.

A further advantage is the method can use a mixture of oligonucleotide primers for the detection of a battery of agents (e.g., pneumonia, mycoplasma, chlamydia, streptococcus, legionella, RSV) suspected of causing a broad range of disease states.

3. Genetic Disease Diagnosis Advantages

The method can be used for the rapid detection of an altered nucleotide base (point mutation) and for the detection of the insertion or deletion of one or more nucleotides in a polynucleotide sequence. In this instance the genetic change has to be known and characterised at the DNA sequence level.

The detection of a single or more base changes can be automated.

The method can be adapted to large scale screening for single (or more) nucleotide changes. This is particularly important in screening for genetic diseases such as cystic fibrosis but can also be adapted to the differentiation of alleles not necessarily involved in gene expression such as used for DNA profiling.

This particular method does not involve solid-liquid hybridization, precise liquid hybridization conditions and is not technically demanding. Other systems, such as Southern blot hybridization, require that the target: polynucleotide sequence is linked to a solid support (technically demanding) and/or the use of oligonucleotide probes that require precise hybridization conditions. These systems cannot be automated and are not easily adapted to large scale screening.

BRIEF DESCRIPTION OF DRAWINGS

Preferred embodiments of the invention are now described with reference to the following drawings in which:

FIG. 4 shows an autoradiograph used to verify the size of the extended oligonucleotide produced in the third example of the invention; and FIG. 5 is a schematic depiction of an apparatus for performing any one of the methods of the invention.

FIG. 6 shows the nucleotide sequences of the primer extension reaction of Example 5. The sequence of the biotinylated specific primer is set out in SEQ ID NO: 7. The sequences of the coding and noncoding strands of the normal CFTR gene segment are set in SEQ ID NO: 8 and 9, respectively, while the sequences of the coding and noncoding strands of the ΔF508 CFTR gene segment are set out in SEQ ID NO: 10 and 11, respectively.

BEST MODE AND OTHER MODES OF CARRYING OUT THE INVENTION

There are four especially preferred applications of the methods of the invention, that is, (i) the detection of a specific nucleotide sequence (major application: infectious diseases) (ii) the detection of a nucleotide or base change (major applications: genetic diseases and DNA fingerprinting) (iii) the detection of multiple specific nucleotide sequences using different capture molecules (major application: multiple infectious diseases) and (iv) detection of multiple nucleotide or base changes in different polynucleotide sequences (major applications: multiple genetic diseases and DNA fingerprinting). A single apparatus (with minor modifications) is suitable for use with all applications.

1. Detection of a specific nucleotide sequence

Figure 1:
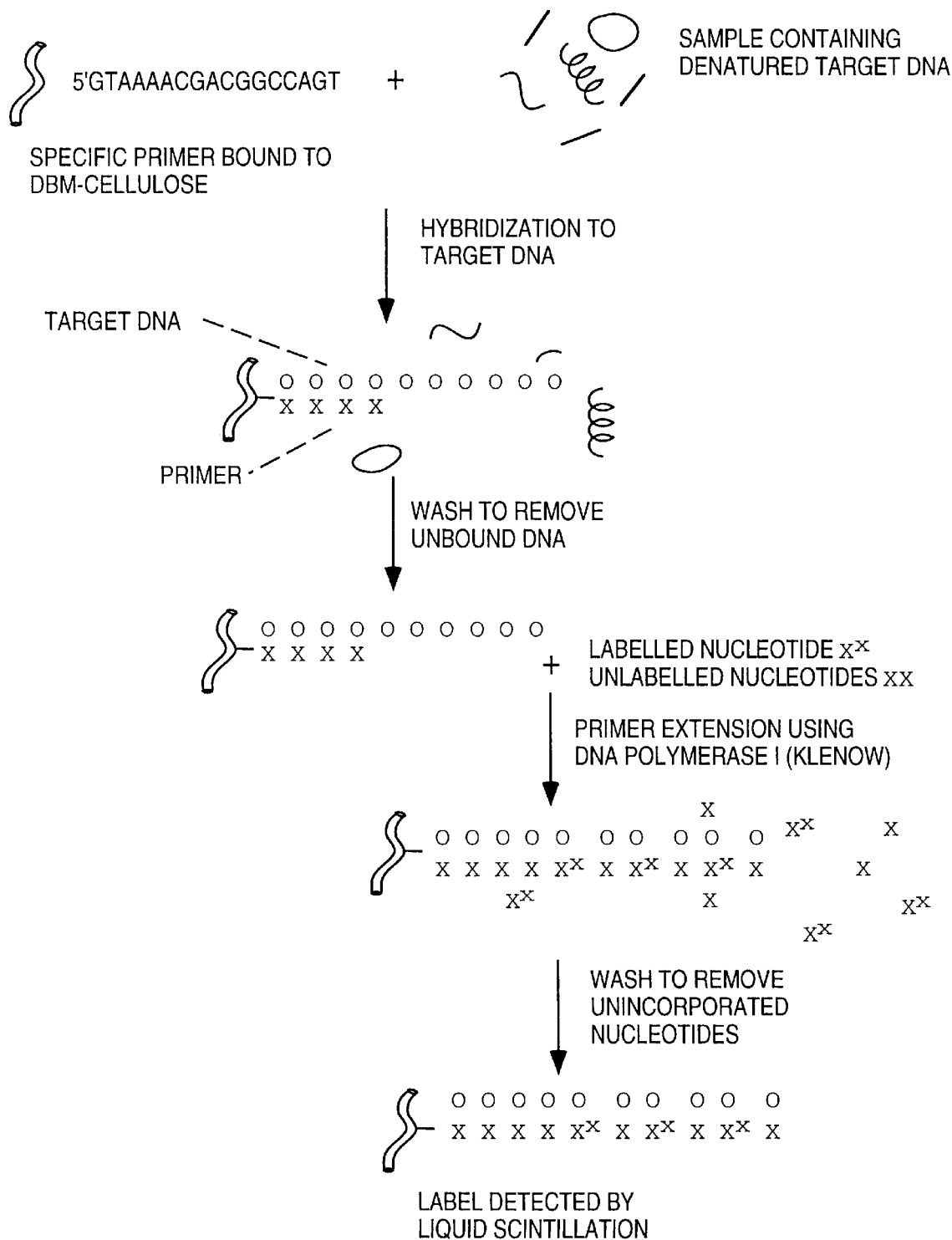
FIG. 1 is a schematic drawing of a method for detecting a specific polynucleotide sequence.

Referring to FIG. 1, a method for detecting a specific polynucleotide sequence first involves the synthesis of an oligonucleotide primer complementary to the target polynucleotide sequence. The optimum length of the primer depends on the length of the most conserved sequence in the polynucleotide sequence to be detected up to a maximum length of 30 nucleotides.

The specific primer is preferably attached to an inert solid support, using the method of Ashley and MacDonald *Analytical Biochem.*, (1984) as described herein below in Example 1. Any inert support particle to which small DNA molecules can be attached can be used, for instance cellulose or nylon. The polynucleotide sequence to be detected is added to the support-specific primer conjugate in the presence of a solution that promotes rapid hybridization between the specific primer and the polynucleotide sequence. One appropriate solution contains 0.15M sodium chloride, 0.015M sodium citrate and 4% polyethylene glycol 6000. The support is then washed.

The choice of washing buffer determines the stringency conditions. A standard buffer is 140 mM sodium chloride, 15 mM sodium citrate and 20 mM sodium phosphate, pH 7.0.

The specific primer is extended using either DNA polymerase I (Klenow fragment) or reverse transcriptase in the presence of the four deoxyribonucleotides, one of which is labelled, radioactively, with biotin or with a fluorescent label. The length of extension depends upon the time and temperature of the extension reaction providing all chemicals are in non-limiting concentration.

Generally the reaction is carried out at 37° C. for 30 minutes and the label is $^{32}$P. The level of incorporation of labelled nucleotide into the extended primer is measured by liquid scintillation when the label is $^{32}$P.

Alternatively the label can be a fluorescent label.

Following primer extension the mixture is washed and assayed for presence of the label.

The presence of label after the final wash indicates that the primer has been extended, and that, therefore, the nucleic acid whose presence is being assayed is present. The specific primer can only be extended using the nucleic acid to which it is complementary as template.

Figure 3A:
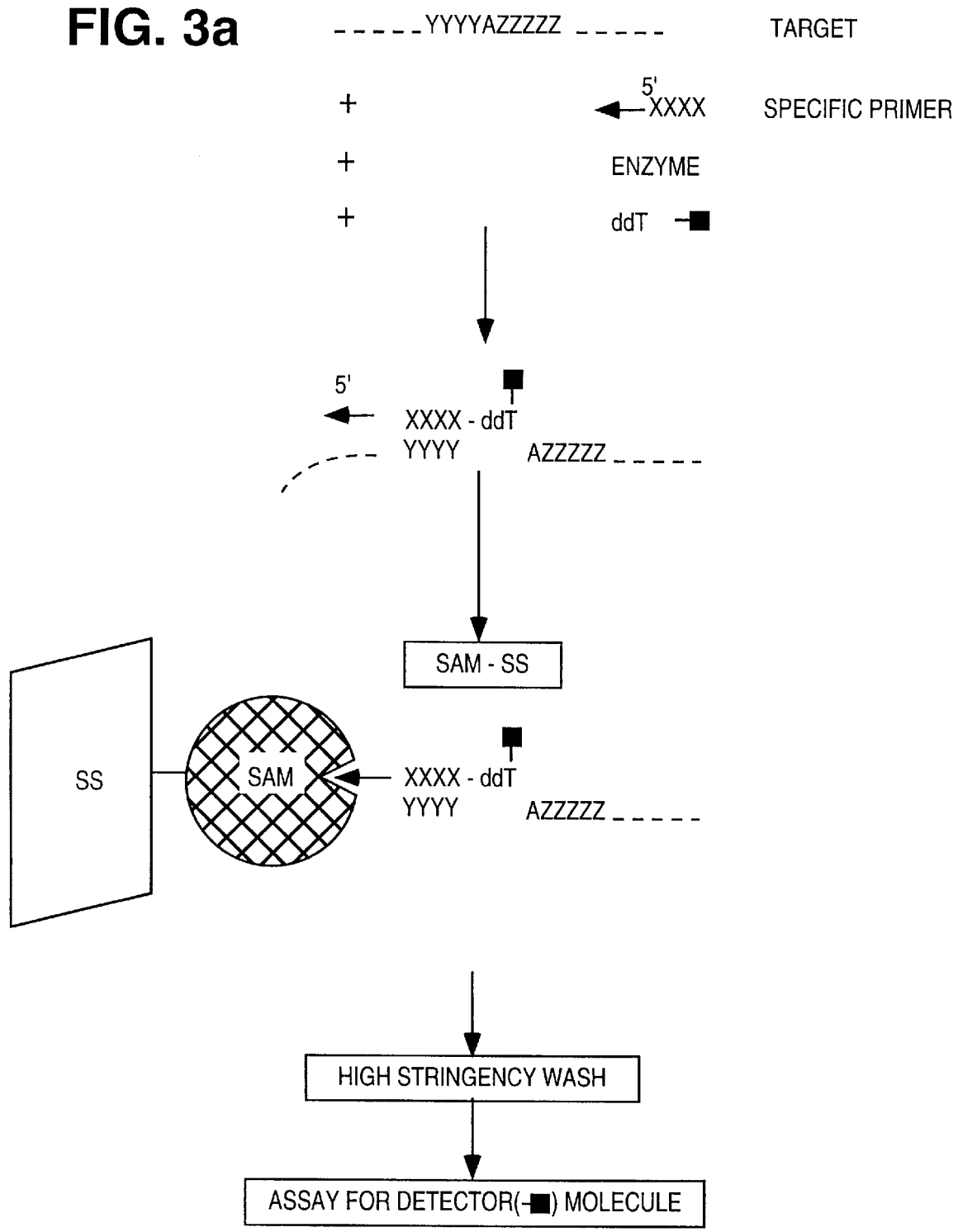
FIG. 3a is a schematic drawing of a method for detecting a nucleotide or base change using a separation element which links to the oligonucleotide primer portion of an extended primer.
Figure 3B:
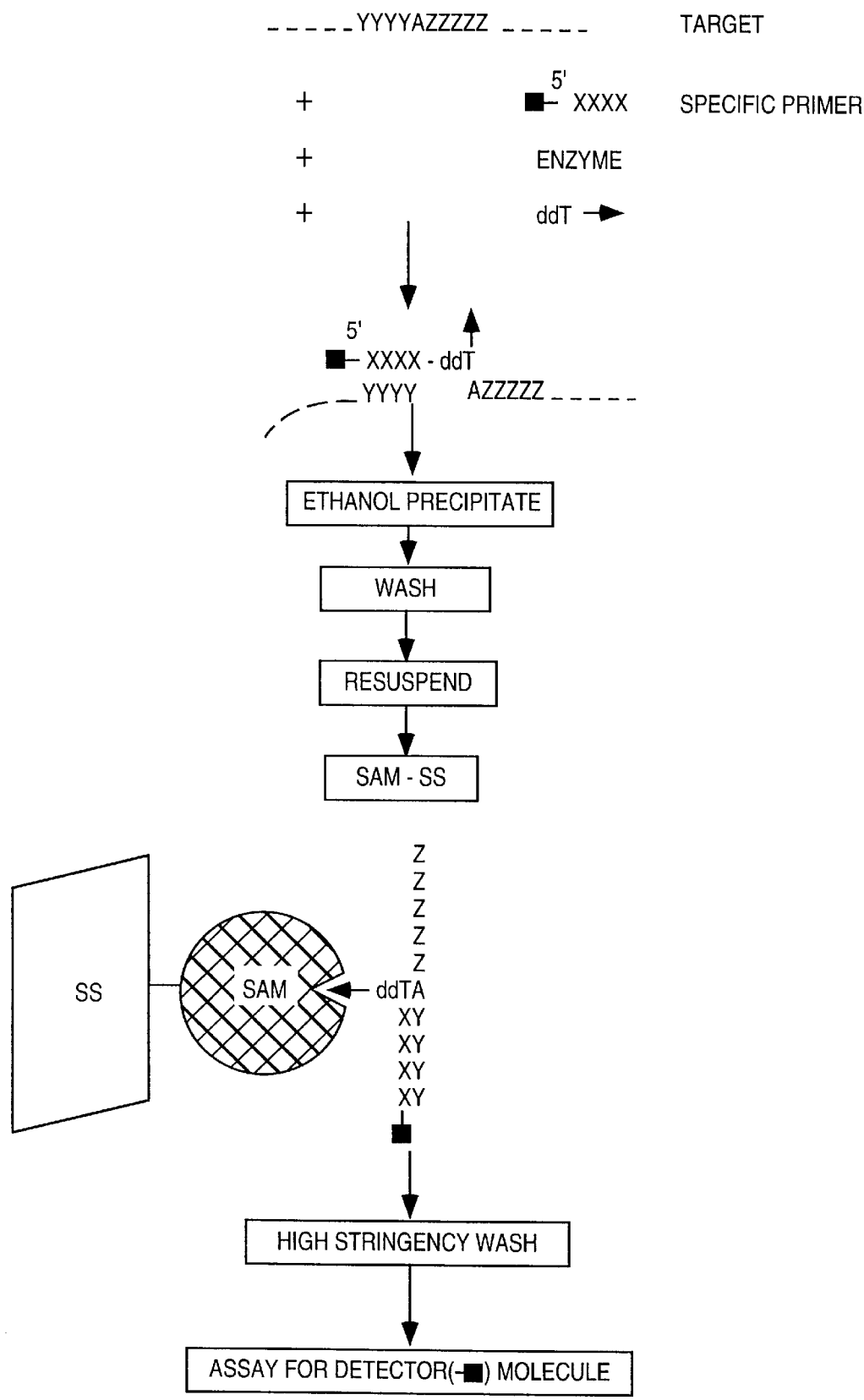
FIG. 3b is a schematic drawing of a method for detecting a nucleotide or base change using a separation element which links to the extended portion of an extended primer.

In summary this method involves the following steps:

the synthesis of a specific primer complementary to part of a known or partly known nucleic acid sequence, the target.

the attachment of a capture (Configuration A-FIG. 2a) or detector (Configuration B-FIG. 2b) molecule to the 5' end of the specific primer the hybridization, in solution, of this specific primer to the target nucleic acid sequence the addition to the solution of the four deoxyribonucleotides and either a DNA dependent DNA polymerase (if the target is DNA) or a RNA dependent DNA polymerase (if the target is RNA) under conditions suitable for the enzymatic extension of the specific primer. One or more of the deoxyribonucleotides has covalently attached to it a detector molecule (Configuration A) or a capture molecule (Configuration B)

the polymerase enzyme extends the primer using the target nucleic acid as a template and simultaneously incorporates either a detector or a capture molecule into the extended primer the reaction can be heat denatured and the cycle repeated to amplify the amount of extended specific primer for Configuration A, the specific affinity molecule (attached to a solid support) is added to the solution under conditions conducive to the binding of the capture molecule to the specific affinity molecule for Configuration B, the extended specific primer is precipitated with ethanol, washed to remove unincorporated deoxyribonucleotide-capture molecule complex. After washing, the extended specific primer is resuspended in a solution conducive to the binding of the capture molecule to the specific affinity molecule. The specific affinity molecule (attached to a solid support) is then added once the extended specific primer is attached to the specific affinity molecule-solid support complex via the capture molecule, the mix is washed extensively under high stringency conditions at the conclusion of the washing step, the mix is assayed using a procedure appropriate for detecting the detector molecule 2. Detection of a nucleotide or base change This method involves the following steps:

the synthesis of a specific primer complementary to part of a known or partly known nucleic acid sequence, the target. The specific primer sequence is complementary to the target sequence either immediately adjacent to but not including the single nucleotide or base to be detected or not immediately adjacent to the single nucleotide or base to be detected but having an intervening sequence between the bound primer and the nucleotide or base to be detected the attachment of a capture (Configuration A-FIG. 3a) or detector (Configuration B-FIG. 3b) molecule to the 5' end of the specific primer. For Configuration C (FIG. 3c), neither a capture or detector molecule are attached to the specific primer at the 5' end the hybridization, in solution, of this specific primer to the target nucleic acid sequence the addition to the solution of only one type of dideoxyribonucleotide (or deoxyribonucleotide), that is, the one which can pair or hydrogen bond with the base or nucleotide to be detected in the target sequence and either a DNA dependent DNA polymerase (if the target is DNA) or a RNA dependent DNA polymerase (if the target is RNA) under conditions suitable for the enzymatic extension of the specific primer. The dideoxyribonucleotide (or deoxyribonucleotide) has covalently attached to it a detector molecule (Configuration A and C) or a capture molecule (Configuration B) the polymerase enzyme extends the primer using the target nucleic acid as a template adding only one molecule of the dideoxyribonucleotide (or deoxyribonucleotide) if base pairing is possible. The specific primer is not extended if base pairing between the dideoxyribonucleotide (or deoxyribonucleotide) and the target sequence is not possible. A detector (Configuration A and C) or a capture (Configuration B) molecule the reaction can be heat denatured and the cycle repeated to amplify the amount of extended specific primer for Configuration A, the specific affinity molecule (attached to a solid support) is added to the solution under conditions conducive to the binding of the capture molecule to the specific affinity molecule for Configuration B, the extended specific primer is precipitated with ethanol, washed to remove unincorporated dideoxyribonnucleotide-capture molecule complex (or deoxyribonucleotide-capture molecule complex). After washing, the extended specific primer is resuspended in a solution conducive to the binding of the capture molecule to the specific affinity molecule. The specific affinity molecule (attached to a solid support) is then added for Configurations A and B. once the extended specific primer is attached to the specific affinity molecule-solid support the complex via the capture molecule, the mix is washed extensively under high stringency conditions for Configuration A and B, at the conclusion of the washing step, the mix is assayed using a procedure appropriate for detecting the detector molecule for Configuration C, the reaction mix is loaded onto a lane of an agarose or polyacrylamide gel of suitable composition, electrophoresed to resolve the extended specific primer-detector molecule complex and finally assayed using a procedure appropriate for detecting the detector molecule. Labelled size standards are normally included in another lane of the gel.

3. Detection of Multiple Specific Nucleotide Sequences using Different Capture Molecules, ie Multiple Infectious Diseases This method involves the following steps:

the synthesis of multiple different specific primers each of which is complementary to a different known nucleic acid sequence, the targets the attachment of different capture molecules to the 5' end of the different specific primers the hybridization, in solution, of these different specific primers (with attached different capture molecules) to the different target nucleic acid sequences to which the different specific primers are complementary the addition to the solution of the four deoxyribonucleotides and either a DNA dependent DNA polymerase (if the targets are all DNA), or a RNA dependent DNA polymerase (if the targets are all RNA) or both polymerases (if the targets are a mixture of both DNA and RNA) under conditions suitable for the enzymatic extension of the specific primers if these specific primers are hybridized with their complementary target nucleic acid sequence. One or more of the deoxyribonucleotides has covalently attached to it a detector molecule the polymerase enzyme(s) extends the different specific primer using the different target nucleic acid sequences as a templates and simultaneously incorporates a detector molecule into the extended primers the reaction can be heat denatured and the cycle repeated to amplify the amount of different extended specific primers different specific affinity molecules (which have specific affinity for the different respective capture molecules and are attached to solid supports such as "test strips") are added to the solution under conditions conducive to the binding of the different capture molecule to their different specific affinity molecule once the different extended specific primers are attached to their specific affinity molecule-solid support complexes via the different capture molecules, each different complex is removed individually with the appropriate test strip which subsequently is washed extensively under high stringency conditions at the conclusion of the washing step, one of the test strips is assayed for the presence of detector molecule using a procedure appropriate for the particular detector molecule. If the assay indicates that the detector molecule Is present on the test strip then this is indicative that the specific nucleotide sequence targeted by the primer having that particular detectable molecule is present in the test sample. If the assay indicates that no detector molecule is present on the test strip then this is indicative that the specific nucleotide sequence targeted by the primer having that particular detectable molecule is not present in the test sample the procedure of the last step is repeated for each of the test strips 4. Detection of a multiple nucleotide or base chances in different polynucleotide sequences, ie multiple genetic defects or diseases This method involves the following steps:

the synthesis of a multiple different specific primers each of which is complementary to a different known nucleic acid sequence, the targets. The different specific primer sequences are complementary to their respective different target sequences immediately adjacent to the single base to be detected the attachment of different capture molecules to the 5' end of the different specific primers the hybridization, in solution, of these different specific primers to their different respective target nucleic acid sequences the addition of the solution of all four types of dideoxyribonucleotide (eg, ddATP, ddCTP, ddGTP, ddTTP) and either a DNA dependent DNA polymerase (if all the targets are DNA) or a RNA dependent DNA polymerase (if all the targets are RNA) or both (if the targets are a mixture of both DNA and RNA) under conditions suitable for the enzymatic extension of the different specific primers. Each dideoxyribonucleotide has covalently attached to it a different detector molecule.

the polymerase enzyme extends the different specific primers using the different target nucleic acid sequences as templates adding only one molecule of one of the dideoxyribonucleotides the reaction can be heat denatured and the cycle repeated to amplify the amounts of extended different specific primers the specific affinity molecules (with specific affinity for the different respective capture molecules and are attached to solid supports such as "test strips") are added to the solution under conditions conducive to the binding of the different capture molecules to the different specific affinity molecules once the different extended specific primers are attached to their specific affinity molecule-solid support complexes via the different capture molecules, each different complex is removed individually with the appropriate test strip which subsequently is washed extensively under high stringency conditions at the conclusion of the washing step, one of the test strips is assayed for the presence of detector molecule using a procedure appropriate for the particular detector molecule. If the assay indicates that the detector molecule is present on the test strip then this is indicative that the specific nucleotide sequence targeted by the primer having that particular detectable molecule is present in the test sample. If the assay indicates that no detector molecule is present on the test strip then this is indicative that the specific nucleotide sequence targeted by the primer having that particular detectable molecule is not present in the test sample the procedure of the last step is repeated for each of the test strips 5. Apparatus for Carrying out Methods of the Invention Referring to FIG. 5 apparatus 100 is generally suitable for carrying out the methods of the invention according to non-automatic or automatic procedures. The extending and separation procedures take place within removable reactor 10 which is disposed within support vessel 11. Vessel 11 is temperature controlled by thermo-controlled jacket 12. The contents of reactor 10 are mixed by shaking vessel 11 using shaker 13. The base of reactor 10 has specific porosity membrane 14 supported by membrane support 15. Reactor 10 is supported in vessel 11 by support for removable reactor 21.

Sample material, primer(s) and extending reagents are delivered to reactor 10 from their respective vessels 16, 17 and 18. Primer annealing and extension are permitted to occur for an appropriate period under gentle mixing and fixed temperature conditions. This reaction creates an extended primer having a detectable element and separation element provided the sample has a specific polynucleotide sequence for which the primer has a sequence complementary to part of the specific polynucleotide sequence.

Subsequently specific affinity molecule(s) (SAM(S)) attached to an inert support for the separation element are added to reactor 10 from SAM supply vessel 19 and allowed to react with extended primer for an appropriate period. Unreacted reagents, buffer and unextended primer(s) are then removed to waste container 25 via vacuum line 25, having associated vacuum pump 24, attached to the base of support vessel 11 whilst extended primer(s) having attached SAM(S) are retained in reactor 10 by membrane 14. The retained primer-SAM complexes are washed with wash reagent supplied from vessel 22 to remove background and thereby create the first fraction in reactor 10. The first fraction is then examined for the presence of detectable element with detector 23. Typically, the detectable element is a radioactive element such as $^{32}P$ and detector 23 is a scintillation counter.

If the assay indicates that the detector molecule is present then this is indicative that the specific nucleotide sequence is present in the test sample. If the assay indicates that no detector molecule is present then this is indicative that the specific nucleotide sequence is not present in the test sample.

EXAMPLE 1

In this example of the detection of a specific polynucleotide sequence, the method depicted in FIG. 1 was used for the detection of the single stranded genomic DNA of the bacteriophage M13.

1. Synthesis of the synthetic primer.

A 17-mer DNA complementary to M13 ssDNA was synthesized on an Applied Biosystems DNA Synthesizer.

The 17-mer had the nucleotide sequence set out in SEQ ID NO: 1:

3'-T—G—A—C—C—G—G—C—A—G—C—A—A—A—A—T—G-5'

This primer Is not only complementary to M13 single-stranded DNA but also to the bacterial double-stranded DNA plasmid, pUC12.

2. Attachment of the Drimer to cellulose.

The method of Ashley and MacDonald (1984) was used to attach the primer to ABM-cellulose. The amino benzyloxymethyl (ABM) groups on ABM cellulose were diazotized to form diazobenzyloxymethyl-cellulose (DBM-cellulose) by suspending the DBM-cellulose in 1.2N HCL containing 0.27 mg $NaNO_2$/ml with stirring at 0° C. for 30 minutes. The specific primer was attached to the DBM-cellulose by adding the primer to the DBM-cellulose suspeneded in 25 mM $NaPO_4$, pH6.5 and incubating overnight at 4° C. Approximately 40 μg of specific primer was bound to 20 mg of cellulose.

3. Hybridization of specific primer-cellulose (SP-cellulose) with target nucleic acid SP-cellulose was resuspended in a solution containing the target nucleic acid either M13 ssDNA or pUC12 and water. This was mixed, boiled for 5 minutes and quenched on ice. The mixture was then washed by centrifugation using a wash buffer comprising 140 mM sodium chloride, 15 mM sodium citrate and 20 mM sodium phosphate, pH 7.0 to remove nucleic acids that had not hybridised with the SP-cellulose.

4. Primer extension

The specific primer was extended using DNA polymerase I (Klenow fragment) together with labelled and non-labelled nucleotides.

The reaction conditions were as follows:

| 20:1 Reaction Mix | |
| --- | --- |
| 50 mM | Tris-HCl, pH 8.3 |
| 8 mM | Magnesium chloride |
| 4 mM | dithiothreitol |
| 4 mM | sodium pyrophosphate |
| 1 mM | each dATP, dGTP and dTTP |
| 1 Ci | $^{32}P$ dCTP |
| 7 units | DNA polymerase I, Klenow fragment. |

It was found that the addition of polyethylene glycol 6000 to a final concentration of 4% increased the incorporation of radioactivity up to three fold.

The reaction mix was incubated for 2 hrs at 20° C.

At the end of the incubation, unincorporated nucleotides were removed by washing the SP-cellulose four times by centrifugation. The washing buffer was 140 mM sodium chloride, 15 mM sodium citrate and 20 mM sodium phosphate, pH 7.0. The sample was vortexed for 1 minute at room temperature then centrifuged at 12,000 g for 5 minutes. This was repeated four times.

Finally, the SP-cellulose was added to a vial containing scintillation solution and incorporation was determined using a liquid scintillation counter.

EXAMPLE 2

In this example of the detection of a specific polynucleotide sequence according to the second embodiment of the invention, single stranded genomic DNA from the bacteriophage M13 mp18 was detected using the following oligonucleotide primer:

```
                            M13 ssDNA
SEQ ID NO:2 3' ... T T T G C T G C C G G T C A C G G T T C G A A ... 5'
SEQ ID NO:3    5' A A A C G A C G G C C A G T G C C
```

Specific Primer

Figure 2A:
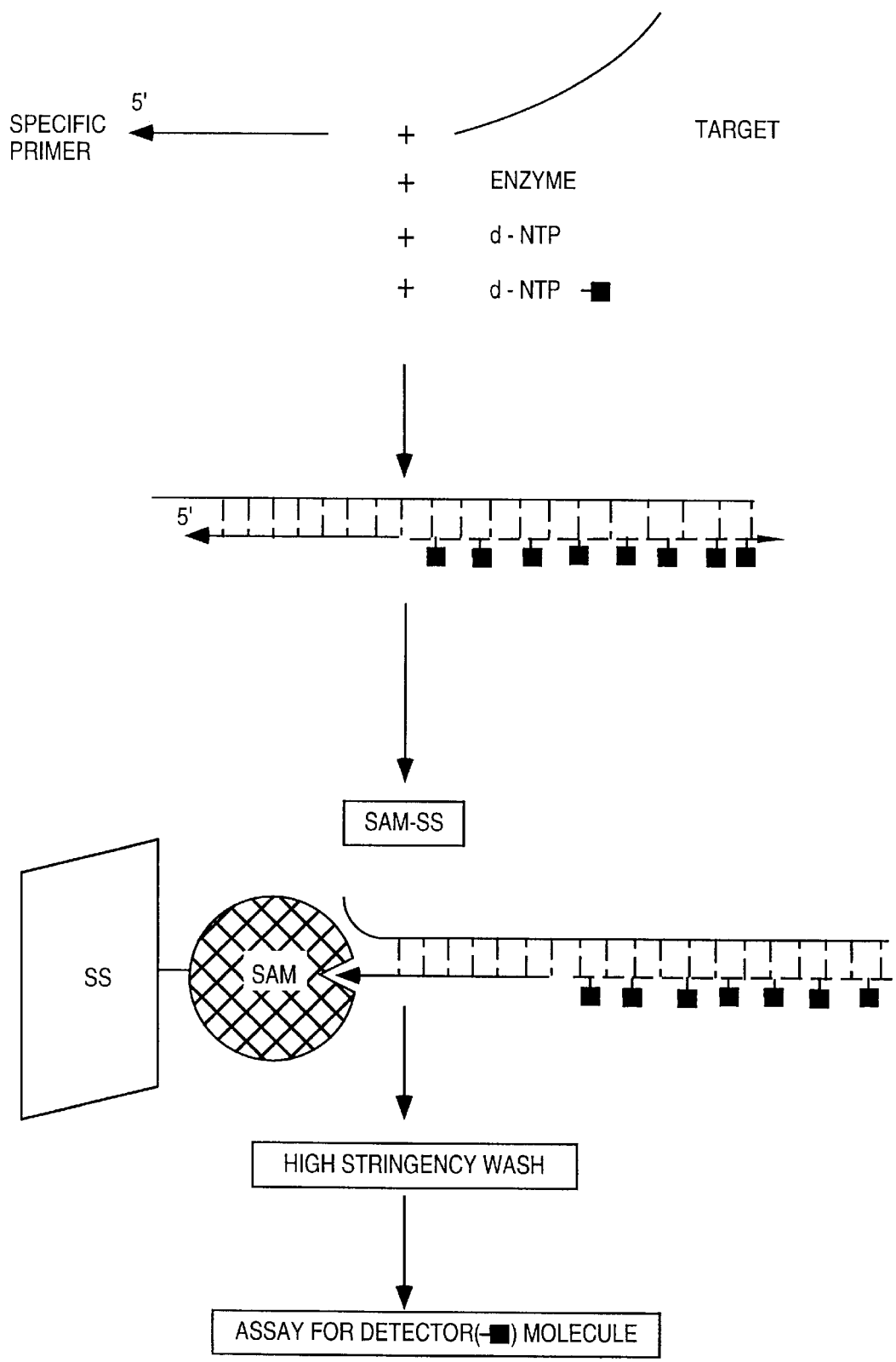
FIG. 2a is a schematic drawing of a method for detecting a specific polynucleotide sequence using a separation element which links to the oligonucleotide primer portion of an extended primer.
Figure 2B:
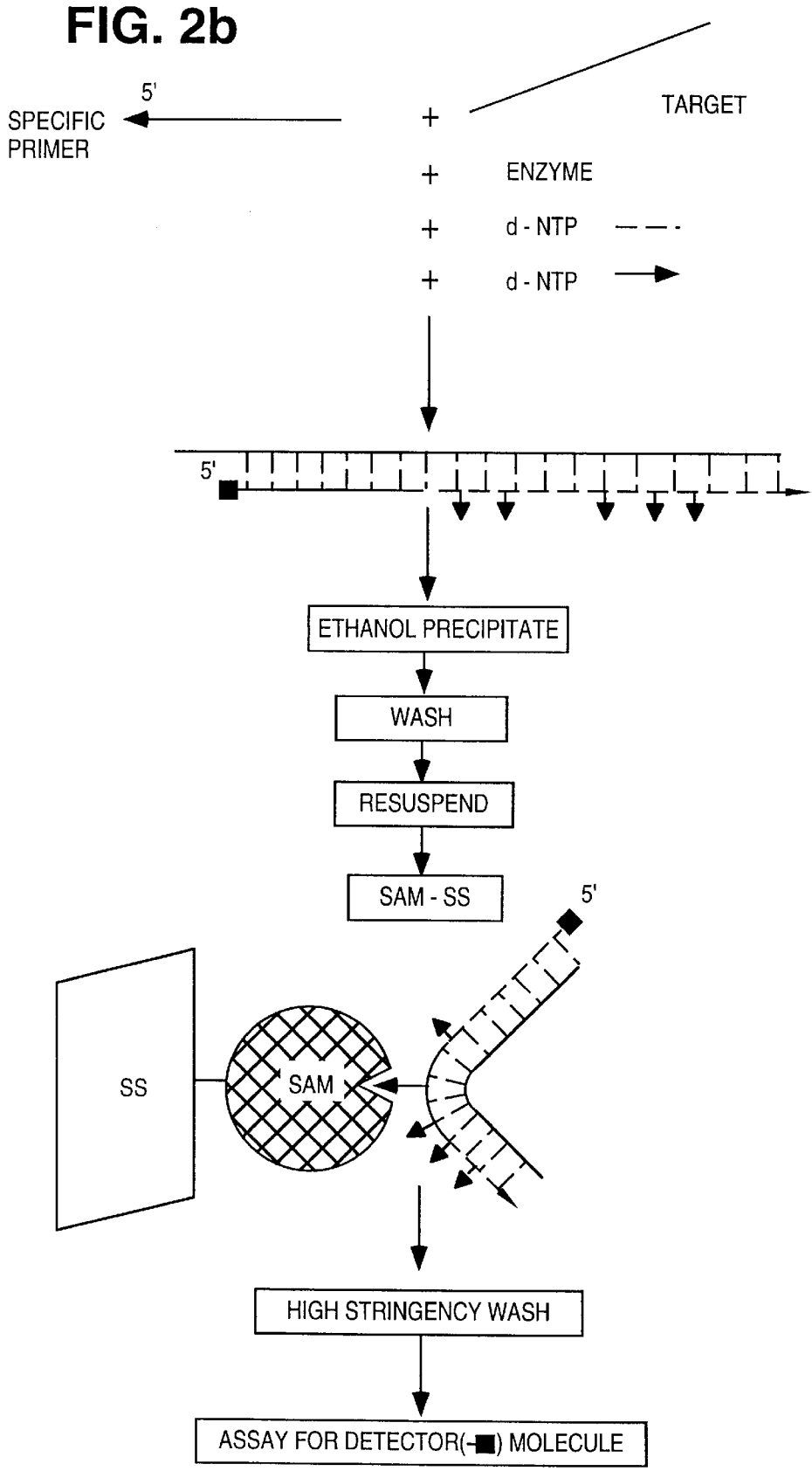
FIG. 2b is a schematic drawing of a method for detecting a specific polynucleotide sequence using a separation element which links to the extended portion of an extended primer.

The configuration used in this example is demonstrated In FIG. 2b; the detector molecule in this example is $^{32}P$ and is attached to the 5' end of the specific primer; the capture molecule is biotin and is incorporated into the extended primer as biotin-16-dUTP (an analogue of dTTP); the specific affinity molecule is streptavidin and the solid support is agarose.

The specific primer was synthesised using an oligonucleotide synthesiser and was 5' end labelled with $^{32}P$ using polynucleotide kinase as follows:

| Reaction mix: | |
|---|---|
| Specific primer (50 pmoles 5'OH ends) | 1 μl |
| 100 mM dithiothreitol | 5 μl |
| 10x TM Buffer | 5 μl |
| (600 mM Tris, pH 7.6; 90 mM MgCl$_2$) | |
| γ-$^{32}$P-dATP (3000 Ci/mmole) | 15 μl |
| T$_4$ polynucleotide kinase (8.6 units/ml) | 2 μl |
| ddH$_2$O | 22 μl |

The reaction mix was incubated at 37° C. for 20 minutes. The labelled primer was separated from unincorporated $^{32}$P using a DEAE cellulose column.

The primer extension reaction was carried using the following reaction mix either with M13 mp18 or lambda bacteriophage (as a non-homologous control):

| | M13 | Lambda |
|---|---|---|
| Template DNA (500 ng) | 2.5 ul | 10 ul |
| $^{32}$P labelled specific primer | 10 ul | 10 ul |
| DNA polymerase (Klenow; 1 unit/ul) | 1 ul | 1 ul |
| Biotin-16-dUTP (1 mM) | 1 ul | 1 ul |
| dCTP (1 mM) | 1 ul | 1 ul |
| dGTP (1 mM) | 1 ul | 1 ul |
| dATP (1 mM) | 1 ul | 1 ul |
| NaCl (5 M) | 1 ul | 1 ul |
| MgSO$_4$ (1 M) | 0.5 ul | 0.5 ul |
| Dithiothreitol (4 mM) | 1.25 ul | 1.25 ul |
| Bovine serum albumin (1 mg/ml) | 2.5 ul | 2.5 ul |
| Tris HCl, pH 7.0 (1 M) | 2.5 ul | 2.5 ul |
| ddH$_2$O | 24.75 ul | 25/25 ul |

The reaction mix was incubated at 37° C. for 60 minutes. At the completion of the incubation, the extended primer was precipitated with ethanol to remove unincorporated biotin-16-dUTP. To the reaction mix was added one volume (50 ul) 5M amnonium acetate and 250 ul ethanol, followed by brief mixing and incubation at −20° C. for one hour. The precipitate was collected by centrifugation, dried briefly, resuspended in 50 ul ddH$_2$O and applied to a 200 ul streptavidin/agarose column (containing 0.12 mg streptavidin) previously equilibrated with binding buffer (10 mM Tris HCl, pH7.5; 200 mM NaCl; 1 mM EDTA). The column was washed five times with 500 ul each of binding buffer. The streptavidin/agarose was suspended in 1 ml binding buffer to which was added 6 ml of scintillation fluid and the mixture counted in a liquid scintillation counter.

The results for the M13 and the lambda systems were as follows:

| Template | cpm |
|---|---|
| M13 | 29,055 |
| lambda | 1,043 |

The results demonstrate that the primer was specifically extended only In the presence of the homologous template, M13, but not extended in the presence of the non-homologous template, lambda. Further, biotin was incorporated Into the extended primer.

EXAMPLE 3

Figure 3C:
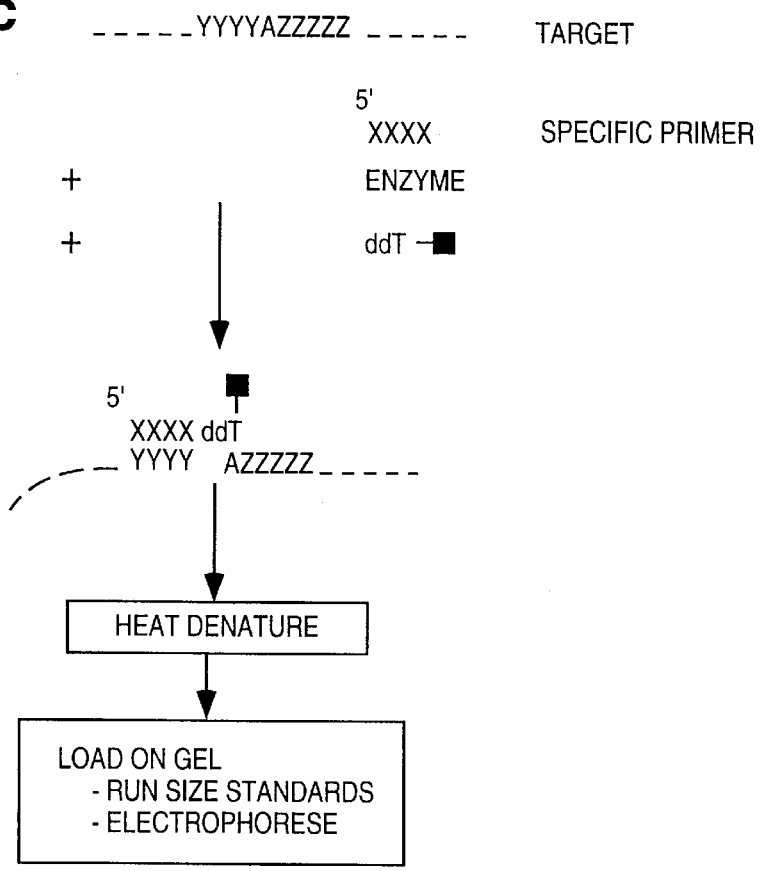
FIG. 3c is a schematic drawing of a method for detecting a nucleotide or base change using a detectable element linked to the extended portion of an extended primer.
Figure 3C:
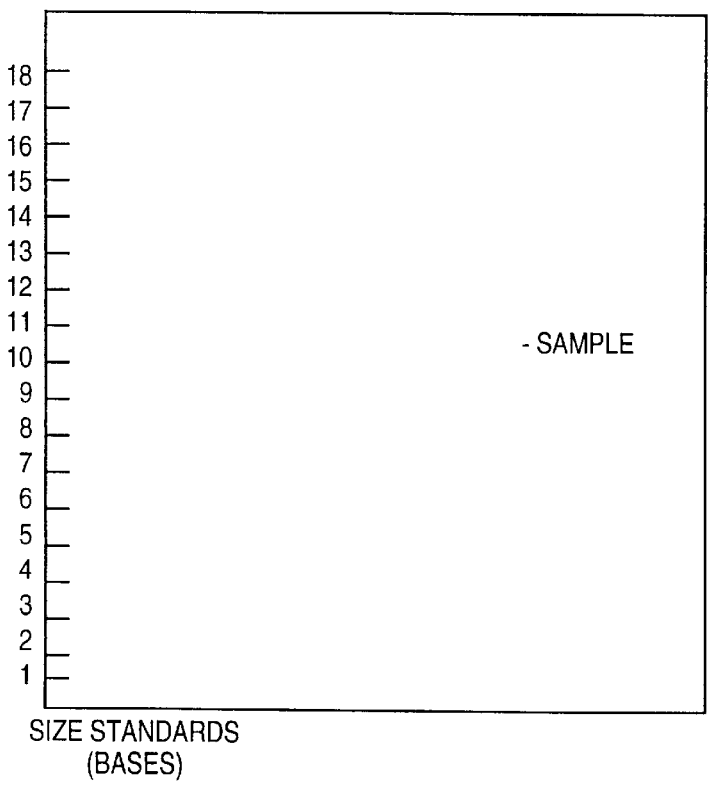

In this example of the use of the invention for the detection of an altered nucleotide base, the configuration shown in FIG. 3c was used. The M13 sequence detected and the oligonucleotide primer sequence used were as follows:

M13 ssDNA
SEQ ID NO:2: 3' ... T T T G C T G C C G G T C A C G G T T C G A A ... 5'
SEQ ID NO:3:   5' A A A C G A C G G C C A G T G C C

Specific Primer

The specific primer was synthesised using an oligonucleotide synthesizer.

The reaction mix was set up as follows:

| | |
|---|---|
| 500 ng M13mp18 ssDNA | 2.5 μl |
| 0.8 pmoles specific primer | 2.0 μl |
| 10x reaction buffer | 1.5 μl |
| ddH$_2$O | 1.0 μl |

This reaction mix was incubated at 55° C. for 10 minutes at which time the following were added:

| | |
|---|---|
| $^{32}$P dATP (3000 Ci/mmole, 10 mCi/ml) | 0.5 μl |
| $^{32}$P ddATP (3000 Ci/mmole, 10 mCi/ml) | 1.5 μl |
| DNA polymerase (Klenow) (1 unit/μl) | 1.0 μl |

This reaction mix was incubated for a further 15 minutes at 25° C. The reaction was stopped by the addition of 4 ul formamide dye (95% formamide, 0.1% xylene cyanol, 0.1% bromophenol blue). The reaction mix was heated at 100° C. for three minutes prior to loading on a 20% polyacrylamide gel and electrophoresing for 30 minutes at 30 milliamps. The gel was then fixed in 10% acetic acid, washed with ddH$_2$O and exposed to X-ray film at −80° C. for 12 hours.

The resulting autoradiograph (FIG. 4) exhibited only one band of 18 nucleotides in length. Thus the primer had been extended by only one nucleotide by the incorporation of a labelled adenine residue and thus detecting a specific single nucleotide in a nucleic acid sequence.

EXAMPLE 4

In this example of the detection of a specific polynucleotide sequence, the method of FIG. 2a was used for detection of the single stranded genomic DNA of the bacteriophage M13.

1. Synthesis of the synthetic primer

A 25-mer DNA complementary to MIS ssDNA was synthesized by Clontec (USA). The 25-mer had the nucleotide sequence set out in SEQ ID NO: 4

5'-X ACG TTG TAA AAC GAC GGC CAG TGC C-3' where X is biotin covalently attached to a modified nucleotide.

2. Hybridisation and primer extension

The primer was mixed with buffer containing either M13 DNA (target) or herring sperm DNA (control) and extended using DNA Polymerase I (Klenow fragment).

Reaction conditions were as follows:

50 mM Tris pH 7.5
10 mM MgCl$_2$
4 mM DTT
100 mM NaCl
50 ug/ml bovine serum albumin
0.02 mM each dATP, dGTP, dTTP 1 Ci $^{32}$P dCTP 742.5 ng/50 ul M13 or herring sperm DNA 25.8 ng/50 ul biotin-primer 0.5 units DNA polymerase I, Klenow fragment.

The reaction mixes were incubated at 37° C. for 60' and terminated by precipitation and washing.

Precipitation was carried out by addition of 5M ammonium acetate, calf thymus DNA as carrier and ethanol. Pellets collected by centrifugation were washed with 70% ethanol until washings contained less than 500 cpm.

Washed pellets were then dissolved in binding buffer consisting of 200 mM NaCl, 10 mM Tris pH 7.5, 1 mM EDTA and applied to a column of streptavidin-agarose. Columns were washed with several volumes of buffer and counts bound to streptavidin agarose (SA) were measured, with the following results:

| Target | cpm bound to SA |
|---|---|
| M13 | 11,939 |
| Herring Sperm | 83 |

The results demonstrate that only primers extended in the presence of target M13 DNA result in significant radioactivity being bound to the column.

EXAMPLE 5

In this example, Configuration A of the procedure of the invention for detection of a modified nucleotide base was supplemented by the following steps: (i) amplification of the target DNA by PCR and purification of the amplified DNA, (ii) rapid annealing of a primer including a capture molecule to the target DNA by quenching in an ethanol/dry ice bath, and (iii) addition of unlabelled dideoxynucleotides during the primer extension reaction to ensure chain termination.

The procedure was utilized in a blind clinical trial to screen human DNA for a codon deletion, the ΔF508 mutation, in the cystic fibrosis transmembrane conductance regulator (CFTR) gene. The ΔF508 mutation is one known mutation which results in cystic fibrosis if the genotype of an individual is homozygous for the mutation. Heterozygosity for the mutation does not result in the cystic fibrosis phenotype. The codon is entirely missing in the mutant gene. The three nucleotides normally encode a phenylalanine which is amino acid 508 of the normal or wild type cystic fibrosis protein.

A blind trial of 69 human blood samples was conducted. The entire screening procedure, including PCR amplification, was independently performed on each sample by two different operators.

1. DNA extraction from blood

Any standard technique may be used for the extraction of DNA from blood samples. Two suitable techniques are described in Singer et al., *Nuc. Acids Res.*, 16, p. 7738 (1988) and Grimberg et al., *Nuc, Acids Res.*, 17, p. 8390 (1989).

2. PCR amplification of target sequence(s)

Polymerase chain reaction procedures were used to amplify the target DNA sequence, a segment of the CFTR gene corresponding to nucleotides 1613 through 1683, the numbering of which refers to the sequence of the normal gene. Depending on the genotype of the patient, the amplification products were either 71-base pair segments corresponding to the normal CFTR gene sequence or 68-base pair segments corresponding to the mutant gene sequence, or both.

A 50 ul reaction mix contained 10 mM Tris, pH 8.0, 1.5 mM MgCl$_2$, 50 mM KCl, 200 uM each of dATP, dCTP, dGTP and dTTP, 50 pmoles each of primer CF1

SEQ ID NO: 5
5'-TTTCCTGGATTATGCCTGGCAC-3' and reverse primer CF2

SEQ ID NO: 6
5'-GTATCTATATTCATCATAGGAAACAC-3', 0.5–1.0 ug genomic DNA and 0.75 units Amplitaq DNA polymerase (Perkin Elmer Cetus). The reaction mix was overlayed with 50 ul paraffin oil. The fragments were amplified using a Perkin Elmer Cetus DNA thermal cycler beginning with a 5 minute denaturation at 95° C., followed by 30 cycles of: 45 second denaturation at 94° C., 1 minute annealing at 45° C. and 1 minute extension at 72° C. The final cycle was completed with a 7 minute extension step at 72° C.

3. Purification of PCR product

Unreacted nucleotides, primers, unamplified genomic DNA and enzymes were separated from the amplified DNA segments using an Isogene Kit (Perkin Elmer Cetus). Briefly, a 45 ul aliquot of the completed PCR mixture was added to 90 ul sodium iodide reagent and the resulting solution was cooled on ice for 5 minutes. DNA binder (10 ul) was then added and the solution gently rotated at room temperature for 10 minutes. The bound DNA was collected by centrifugation at 12,000 g for 5 minutes. The supernatant was discarded and the pellet was washed three times with 200 ul wash buffer (10 mM Tris, pH 7.5, 10 mM NaCl, 1 mM EDTA, 70% ethanol) by vortexing and centrifugation. The DNA was eluted from the final pellet with two washes of 20 ul distilled water.

4. Synthesis of biotinylated specific primer

A forty base oligonucleotide specific to base numbers 1613 through 1652 of the normal CTFR gene was synthesized on an Applied Biosystems (ABI) PCR-Mate DNA Synthesizer Model 391. Aminolink 2 (ABI) was used to introduce a single amino group at the 5' terminus of the primer in the final coupling cycle. Biotin was coupled to this 5' amino group by dissolving 50 ug of the unpurified amino-modified 40mer in 300 ul 0.25M Tris-HCl, pH 8.5. 300 ul 15 mM biotinamidocaproate N-hydroxysuccinimidester in 50% dimethylformamide was then added to the solution and incubated at 25° C. for 16 hours. The solution was then concentrated to approximately 100 ul and the biotinylated primer purified by reverse phase HPLC.

The sequence of the biotinylated specific primer was:
SEQ ID NO: 7
Biotin-5 'TTTCCTGGATTATGCCTGGCACCAT-TAAAGAAAATATCAT 3'.

5. Primer extension reaction

An aliquot of 3 ul of the purified PCR product of each blood sample was added to each of two Eppendorf tubes containing biotinylated specific primer (BSP-1) (1 pmole), 2 ul 5× extension buffer (200 mM Tris-HCl, pH 7.5; 100 mM MgCl$_2$, 250 mM NaCl), 1 ul 5% Tween 20/polyoxyethylene sorbitanmonolaurate Nonidet P40 (ethyphenylpolyethyleneglycol) (1:1 v/v) to a total volume of 10 ul. The solutions were boiled for three minutes and immediately quenched in an ethanol/dry ice bath. 4.5 ul of either "C termination mix" (22 mM DTT, 33 mM sodium isocitrate, 22 mM MnCl$_2$, 0.72% Tween 20/Nonidet P40

(1:1 v/v), 55 uM each of ddATP, ddGTP, and ddTTP, and 1.1 uM $^{35}$S ddCTP) or "T termination mix" (22 mM DTT, 33 mM sodium isocitrate, 22 mM MnCl$_2$, 0.72% Tween 20/Nonidet P40 (1:1 v/v), 55 uM each of ddATP, ddCTP, and dd GTP, and 1.1 uM $^{35}$S ddTTP) was then added to each Eppendorf tube and the mixtures were thawed on ice. The BSP-1 was extended by one dideoxynucleotide through the addition of 2 units T7 DNA polymerase and incubation for 5 minutes at 37° C. The mixture was again placed on ice.

The products of the extension reaction are diagrammed in FIG. 6. Briefly, if only the normal gene is present (i.e., the patient is homozygous normal), a radiolabelled C will be added in the first aliquot; if only the mutant gene is present (i.e., the patient is homozygous for the mutation), a radiolabelled T will be added in the second aliquot; and, if the sample derives from a genetically heterozygous patient, extension will occur in both aliquots.

6. Washing of beads and analysis

A 15 ul aliquot of Dynabeads M-280 Streptavidin (10 mg/ml) (Dynal A.S., Oslo) was washed twice, each time with 250 ul 4×SSPE (4×SSPE; 600 mM NaCl, 40 mM NaH$_2$PO$_4$, 4 mM EDTA, pH 7.4)/0.1% SDS. The extended BSP-1 solution was added to the Dynabead pellet together with 100 ul 4×SSPE/0.1% SDS. This mixture was rotated for 30 minutes at 27° C. The tube was then placed in a Magnetic Particle Concentrator (Dynal A.S.) for 30 seconds before the supernatant was removed. The Dynabeads were then washed an additional 12 times each with 250 ul 4×SSPE/0.1% SDS, rotated for 3 minutes at 27° C. and the supernatant was discarded. Finally, the beads were resuspended in 100 ul 4×SSPE/0.1% SDS and counted in a liquid scintillation counter.

7. Results

The prediction of genotype for each sample (patient) was based on the counts obtained for the product of the primer extension reaction using the C termination mix (contained $^{35}$S ddCTP) compared to the counts obtained for the product of the parallel primer extension reaction using the T termination mix (contained $^{35}$S ddTTP). The ratio C:T is the number of cpm incorporated into the primer as $^{35}$S ddCTP divided by the number of cpm incorporated into the primer as $^{35}$S ddTTP.

Theoretically, the following ratio values (of C:T incorporation) and corresponding genotype predictions may be determined from the raw cpm data generated by the screening method:

| Genotype Prediction | Ratio Value |
|---|---|
| Homozygous normal (−/−) | ∞ |
| Heterozygous (+/−) | 1 |
| Homozygous mutation (+/+) | 0 |

The ratio values determined from the raw cpm data (without subtracting background counts) generated by the trial screening for the ΔF508 mutation actually fell into the following ranges:

| Homozygous normal (−/−) | >2,395 |
|---|---|
| Heterozygous (+/−) | 0.359–1.274 |
| Homozygous 508 deletion (+/+) | <0.1. |

The ratio values and genotype prediction for each sample in the trial are presented below in Table 1, wherein the cpm values obtained by the first operator are given in the first row for each sample and the cpm values obtained by the second operator are given in the second row for each sample.

TABLE 1

| SAMPLE NO. | C:T RATIO | GENOTYPE PREDICTION |
|---|---|---|
| CF 1 | 0.632 (Operator 1) | +/− |
|  | 0.832 (Operator 2) |  |
| CF 2 | 0.012 | +/+ |
|  | 0.083 |  |
| CF 3 | 0.014 | +/+ |
|  | 0.084 |  |
| CF 4 | 8.710 | −/− |
|  | 2.661 |  |
| CF 5 | 4.221 | −/− |
|  | 4.034 |  |
| CF 6 | 0.011 | +/+ |
|  | 0.045 |  |
| CF 8 | 0.016 | +/+ |
|  | 0.027 |  |
| CF 9 | 0.015 | +/+ |
|  | 0.044 |  |
| CF 11 | 0.013 | +/+ |
|  | 0.044 |  |
| CF 12 | 0.011 | +/+ |
|  | 0.043 |  |
| CF 13 | 3.249 | −/− |
|  | 7.413 |  |
| CF 14 | 0.011 | +/+ |
|  | 0.035 |  |
| CF 16 | 9.109 | −/− |
|  | 7.369 |  |
| CF 18 | 0.730 | +/− |
|  | 0.572 |  |
| CF 20 | 0.019 | +/+ |
|  | 0.033 |  |
| CF 21 | 0.023 | +/+ |
|  | 0.041 |  |
| CF 23 | 6.455 | −/− |
|  | 3.336 |  |
| CF 24 | 0.788 | +/− |
|  | 0.610 |  |
| CF 25 | 0.953 | +/− |
|  | 0.689 |  |
| CF 28 | 0.723 | +/− |
|  | 0.620 |  |
| CF 29 | 16.523 | −/− |
|  | 9.603 |  |
| CF 30 | 12.726 | −/− |
|  | 4.650 |  |
| CF 31 | 6.966 | −/− |
|  | 4.696 |  |
| CF 32 | 0.680 | +/− |
|  | 0.509 |  |
| CF 33 | 0.573 | +/− |
|  | 0.594 |  |
| CF 34 | 12.390 | −/− |
|  | 5.083 |  |
| CF 37 | 0.809 | +/− |
|  | 0.608 |  |
| CF 38 | 8.914 | −/− |
|  | 5.433 |  |
| CF 39 | 0.621 | +/− |
|  | 0.788 |  |
| CF 40 | 1.274 | +/− |
|  | 0.582 |  |
| CF 41 | 0.010 | +/+ |
|  | 0.040 |  |
| CF 42 | 14.583 | −/− |
|  | 7.896 |  |
| CF 97 | 0.012 | +/+ |
|  | 0.049 |  |
| CF 98 | 0.015 | +/+ |
|  | 0.017 |  |
| CF 99 | 0.577 | +/− |
|  | 0.623 |  |
| CF 100 | 0.591 | +/− |
|  | 0.662 |  |
| CF 101 | 0.720 | +/− |
|  | 0.659 |  |
| CF 102 | 0.741 | +/− |
|  | 1.010 |  |

TABLE 1-continued

| SAMPLE NO. | C:T RATIO | GENOTYPE PREDICTION |
|---|---|---|
| CF 103 | 0.020 0.014 | +/+ |
| CF 104 | 0.777 0.853 | +/− |
| CF 106 | 9.449 3.498 | −/− |
| CF 107 | 5.298 4.946 | −/− |
| CF 111 | 6.118 10.446 | −/− |
| CF 112 | 9.435 9.597 | −/− |
| CF 113 | 0.651 0.697 | +/− |
| CF 114 | 0.604 0.589 | +/− |
| CF 115 | 0.682 0.760 | +/− |
| CF 116 | 5.925 9.813 | −/− |
| CF 117 | 0.716 0.628 | +/− |
| CF 118 | 9.108 10.006 | −/− |
| CF 119 | 0.635 0.375 | +/− |
| CF 141 | 10.694 4.679 | −/− |
| CF 143 | 0.473 0.359 | +/− |
| CF 144 | 12.137 2.395 | −/− |
| CF 145 | 0.429 0.415 | +/− |
| CF 146 | 10.244 8.381 | −/− |
| CF 147 | 0.511 0.442 | +/− |
| CF 161 | 0.650 0.743 | +/− |
| CF 164 | 0.755 0.522 | +/− |
| CF 172 | 0.018 0.032 | +/+ |
| CF 173 | 0.745 0.623 | +/− |
| CF 174 | 7.596 5.559 | −/− |
| CF 180 | 0.558 0.868 | +/− |
| CF 182 | 7.015 6.985 | −/− |
| CF 184 | 0.577 0.685 | +/− |
| CF 194 | 5.508 4.445 | −/− |
| CF 195 | 6.222 5.968 | −/− |
| CF 199 | 0.684 0.616 | +/− |
| CF 220 | 8.685 6.470 | −/− |

The genotype of the individuals from whom the samples were obtained had been previously analyzed by an alternate technique as described in Ballabio et al., *Nature*, 343, p. 220 (1990). The above predictions of genotype as determined by a method of the invention had a 100% correspondence to the results of the alternate technique.

EXAMPLE 6

In this example, the procedure of Example 5 for detection of an altered nucleotide or base was modified to a more readily automatable format by the elimination of the separate step of purification of PCR products and by a reordering of the steps involving reacting the target DNA molecules, the primers including capture molecules, and the ligands for the capture molecules together before primer extension.

The modified procedure was utilized to rescreen the 69 blood samples of Example 5 for the ΔF508 mutation. DNA extraction from the blood samples and PCR amplification of target DNA sequence(s) were the same as in Example 5.

1. Preparation of samples for primer extension

Eppendorf tubes containing 15 ul of Dynabeads M-280 Streptavidin (10 mg/ml) were prepared. The beads were washed twice, each time with 250 ul 4×SSPE. The tubes were then placed in a concentrator to aggregate the beads and form a pellet.

Concurrently, for each blood sample, a 3 ul aliquot of the PCR product (target DNA) was added to each of two 10 ul mixtures containing 1 pmole biotinylated primer (BSP-1), 2 ul 5×extension buffer, 1 ul 5% Tween 20/Nonidet NP40 (1:1 v/v) and distilled water. The mixtures were microfuged briefly, boiled for 3 minutes and immediately quenched in an ethanol/dry ice bath.

The PCR product mixtures were then thawed at room temperature and each was added to a separate Eppendorf tube containing a pellet of Dynabeads. The mixture tubes were each washed with 100 ul of 4×SSPE/0.1% SDS and the wash was added to the respective bead suspension. The suspensions were rotated for 30 minutes at room temperature. The beads were then aggregated and washed 6 times, each time with 250 ul 4×SSPE/0.1% SDS. Next, 250 ul Sequenase wash buffer was added to each tube and the tubes were rotated for 4 minutes at room temperature. The beads were aggregated and the supernatent was removed. This wash step was also repeated a total of six times.

2. Primer extension reaction 4.5 ul "C termination mixes" and "T termination mixes" were prepared as follows:

|  | ddC mix | ddT mix |
|---|---|---|
| 0.1 M DTT | 1 ul | 1 ul |
| 0.1 M MnCl$_2$, 0.15 M Isocitrate | 1 ul | 1 ul |
| 5% Tween 20/Nonidet NP 40 | 0.65 ul | 0.65 ul |
| cold ddCTP (250 uM) | — | 1 ul |
| cold ddTTP (250 uM) | 1 ul | — |
| $^{35}$S ddCTP (10 uM) | 0.5 | — |
| $^{35}$S ddTTP (10 uM) | — | 0.5 ul |
| distilled water | 0.35 ul | 0.35 ul, | and 10 ul buffer mixes were prepared from 1 ul 5% Tween 20/NP 40, 2 ul 5×Sequenase buffer and 7 ul distilled water.

To each bead pellet prepared in section 1 was added: 10 ul buffer mix, 4.5 ul of either the C termination mix or the T termination mix and 2 ul Sequenase enzyme (1 U/ul). The tubes were incubated at 37° C. for 10 minutes with rotation. The beads were then washed at 25° C. with: (i) 250 ul 0.15M NaOH for 5 minutes, (ii) 250 ul 0.1M NaOH for 4 minutes, (iii) 250 ul ddH$_2$O for 4 minutes, and (iv) 9 times with 250 ul 4×SSPE/0.1% SDS for 4 minutes. The beads were aggregated and the supernatent removed after each wash. The resulting pellets were resuspended in 100 ul 4×SSPE/0.1% SDS and added to scintillation vials. The tubes were washed with 4×SSPE/0.1% SDS and the wash was also added to the respective scintillation vial.

The primer extension samples were then counted and the raw cpm data was used to calculate a C:T ratio for each blood sample. The ratios and corresponding genotype predictions are set in Table 2 below.

TABLE 2

| SAMPLE NO. | C:T RATIO | GENOTYPE PREDICTION |
|---|---|---|
| CF 1 | 1.448 | +/− |
| CF 2 | 0.116 | +/+ |
| CF 3 | 0.087 | +/+ |
| CF 4 | 11.930 | −/− |
| CF 5 | 6.407 | −/− |
| CF 6 | 0.095 | +/+ |
| CF 8 | 0.077 | +/+ |
| CF 9 | 0.081 | +/+ |
| CF 11 | 0.067 | +/+ |
| CF 12 | 0.039 | +/+ |
| CF 13 | 13.200 | −/− |
| CF 14 | 0.046 | +/+ |
| CF 16 | 12.495 | −/− |
| CF 18 | 1.311 | +/− |
| CF 20 | 0.047 | +/+ |
| CF 21 | 0.054 | +/+ |
| CF 23 | 7.461 | −/− |
| CF 24 | 0.999 | +/− |
| CF 25 | 1.146 | +/− |
| CF 28 | 1.164 | +/− |
| CF 29 | 6.254 | −/− |
| CF 30 | 9.903 | −/− |
| CF 31 | 17.026 | −/− |
| CF 32 | 1.197 | +/− |
| CF 33 | 1.062 | +/− |
| CF 34 | 5.553 | −/− |
| CF 37 | 0.815 | +/− |
| CF 38 | 4.134 | −/− |
| CF 39 | 1.100 | +/− |
| CF 40 | 0.713 | +/− |
| CF 41 | 0.073 | +/+ |
| CF 42 | 11.665 | −/− |
| CF 97 | 0.006 | +/+ |
| CF 98 | 0.035 | +/+ |
| CF 99 | 0.824 | +/− |
| CF 100 | 0.855 | +/− |
| CF 101 | 0.738 | +/− |
| CF 102 | 0.695 | +/− |
| CF 103 | 0.043 | +/+ |
| CF 104 | 0.557 | +/− |
| CF 106 | 15.057 | −/− |
| CF 107 | 9.005 | −/− |
| CF 111 | 10.789 | −/− |
| CF 112 | | |
| CF 113 | 1.062 | +/− |
| CF 114 | 0.633 | +/− |
| CF 115 | 0.959 | +/− |
| CF 116 | 11.066 | −/− |
| CF 117 | 0.796 | +/− |
| CF 118 | 12.149 | −/− |
| CF 119 | 0.737 | +/− |
| CF 141 | 7.047 | −/− |
| CF 143 | 0.608 | +/− |
| CF 144 | 5.993 | −/− |
| CF 145 | 1.040 | +/− |
| CF 146 | 4.898 | −/− |
| CF 147 | 0.758 | +/− |
| CF 161 | 1.034 | +/− |
| CF 164 | 0.867 | +/− |
| CF 172 | 0.096 | +/+ |
| CF 173 | 0.961 | +/− |

TABLE 2-continued

| SAMPLE NO. | C:T RATIO | GENOTYPE PREDICTION |
|---|---|---|
| CF 174 | 5.721 | −/− |
| CF 180 | 0.803 | +/− |
| CF 182 | 7.902 | −/− |
| CF 184 | 0.773 | +/− |
| CF 194 | 5.754 | −/− |
| CF 195 | 5.591 | −/− |
| CF 199 | 0.514 | +/− |
| CF 220 | 15.765 | −/− |

A ratio value for blood sample CF 112 was not calculated because the counts for both primer extension reactions were below 5000 cpm, indicating that the readings may not have been reliable. The ratio values that were determined from the raw cpm data generated by the rescreening fell into the following ranges:

| Genotype Prediction | Ratio Value |
|---|---|
| Homozygous normal | >4.134 |
| Heterozygous | 0.557–1.448 |
| Homozygous 508 deletion | <0.116. |

The above predictions of genotype for each patient were in 100% agreement with the results of the alternate technique, referenced in Example 5, and with the results of the procedure of Example 5.

While the invention has been described in terms of specific examples and preferred embodiments, it is understood that variations and improvements will occur to those skilled in the art. Therefore, it is intended that the claims cover all such equivalent variations and improvements which come within the scope of the invention as claimed. For instance, while Examples 5 and 6 specifically address detection of a variant DNA sequence involving a codon deletion, it will be apparent that the procedures of these examples are equally applicable to detection of a single base variation in an RNA or DNA sequence.

Industrial Applicability

The method of the invention can be readily used in the following applications:

a) the simple, rapid, sensitive and automatable detection of infectious diseases of humans, animals and plants;

b) the specific, rapid and large scale detection of base changes in nucleic acid sequences, particularly in the detection of gene defects and DNA fingerprinting;

c) kits for use with the above applications; and d) automated equipment for use with the above applications.

We claim:

1. A method for detecting whether a specific nucleotide or base is at a particular position in a specific polynucleotide sequence comprising:

a) exposing, under hybridizing conditions, said specific polynucleotide sequence to an oligonucleotide primer wherein said primer has a sequence complementary to part of the specific polynucleotide sequence wherein said primer has incorporated at its 5' end an element selected from the group consisting of a separation element and a detectable element, and wherein said primer hybridizes at a location selected from the group consisting of (i) immediately adjacent to the particular position and (ii) not immediately adjacent to the particular position whereby there is an intervening sequence between the particular position and primer bound to the specific polynucleotide sequence;

b) extending said hybridized primer up to and including said specific nucleotide or base wherein the 3' terminal nucleotide is a ddNTP and further includes an element selected from the group consisting of a separation element and a detectable element with the proviso that said extended primer has at least one separation element and at least one detectable element;

c) separating the product of step b) into fractions wherein one said fraction contains the primer extension product that contains the chain terminating nucleotide at said particular position; and d) determining whether said primer extension product having said chain terminating nucleotide at said particular position is present in said fraction by assaying said fraction wherein the assay does not include a digestion step.

2. The method of claim 1 wherein said separating step comprises: contacting any extended primer with a molecule having affinity for the separation element, said molecule being linked to a support that facilitates said separating; and separating said contacted extended primer to provide said fraction.

3. The method of claim 2 wherein said separation element and said molecule are selected from the group listed as follows:

| Separation Element | Molecule Having Affinity for Separation Element |
|---|---|
| (a) a ligand for which there is a specific | a specific receptor for the ligand; |
| (b) a specific receptor; | the ligand for the specific receptor; |
| (c) an antigen; | a specific antibody of the antigen; |
| (d) a specific antibody for antigen; | the antigen; |
| (e) an antiidiotypic antibody; | a specific antibody of the antiidiotypic antibody; |
| (f) an antibody for an antiidiotypic antibody; | an antiidiotypic antibody specific for the antibody; |
| (g) a haptenic group; | a specific antibody of the haptenic group; |
| (h) a specific antibody for a haptenic group; | the haptenic group; |
| (i) an enzyme; | a tight binding inhibitor for the enzyme; and |
| (j) a tight binding inhibitor for an enzyme; | the enzyme. |

4. The method of claim 2 wherein said support is a test strip.

5. A method for detecting whether the same or different specific nucleotides or bases are at particular positions in at least two different specific polynucleotide sequences comprising:

a) exposing, under hybridizing conditions, said specific polynucleotide sequences to at least two different oligonucleotide primers, wherein each of said different oligonucleotide primers has a sequence complementary to part of one of said different specific polynucleotide, sequences wherein:

each of said primers hybridizes to its complementary polynucleotide sequence when present in said material, each of said oligonucleotide primers hybridizing to part of a different specific polynucleotide sequence to that of the other primer(s), each of said primers hybridizes to its complementary specific polynucleotide sequence in said material a location selected from the group consisting of (i) immediately adjacent to the particular position and (ii) not immediately adjacent to the particular position whereby there is an intervening sequence between the particular position and primer hybridized to the specific polynucleotide sequence, and each of said primers has incorporated at their 5' end an element selected from the group consisting of a separation element and a detectable element;
b) extending said hybridized different oligonucleotide primers up to and including said specific nucleotide or base wherein the 3' terminal nucleotide is a ddNTP and further includes an element selected from the group consisting of a detectable element and a separation element, with the proviso that each of said extended primers has at least one separation element and at least on detectable element;
c) separating the product(s) of step b) into fractions wherein one said fraction contains the primer extension product(s) that contain the chain terminating nucleotide at said particular position; and
d) determining whether any of said primer extension product having said chain terminating nucleotide at said particular position is present in said fraction by assaying said fraction wherein the assay does not include a digestion step.

6. A screening method for detecting whether the same or different specific nucleotides or bases are at particular positions in at least two different specific polynucleotide sequences comprising:
a) exposing, under hybridizing conditions, said specific nucleotide sequences to at least two different oligonucleotide primers, each of said different oligonucleotide primers having a sequence complementary to part of one of said different specific polynucleotide sequences wherein:
each of said primers hybridize to its complementary polynucleotide sequence when present in said material, each of said oligonucleotide primers hybridizing to part of a different specific polynucleotide sequence to that of the other primer(s),
each of said primers hybridizes to its complementary specific polynucleotide sequence in said material at a location selected from the group consisting of (i) immediately adjacent to the particular position and (ii) not immediately adjacent to the particular position whereby there is an intervening sequence between the particular position and primer hybridized to the specific polynucleotide sequence when presenting said material; and
each of said primers has incorporated at their 5' end an element selected from the group consisting of a separation element and a detectable element;
b) extending said hybridized different oligonucleotide primers up to and including said specific nucleotide or bas e wherein the 3' terminal nucleotide is a ddNTP and further includes an element selected from the group consisting of a detectable element and a separation element with the proviso that each of said extended primers as at least one separation element and at least one detectable element;
c) separating the product(s) of step b) into fractions wherein one said fraction contains the primer extension product(s) that contain the chain terminating nucleotide at said particular position; and
d) determining whether at least one of said primers extension products having said chain terminating nucleotide at said particular position is present in said fraction by assaying said fraction wherein the assay does not include a digestion step.

7. The method of any one of claims 1, 5, or 6 wherein said primer binds to part of said specific polynucleotide in said material immediately adjacent to the particular position.

8. The method of any one of claims 1, 5, or 6 wherein said primer binds to part of said specific nucleotide sequence in said material not immediately adjacent to the particular position whereby there is an intervening sequence between the particular position and primer bound to the specific polynucleotide sequence.

9. The method of any one of claims 1, 5, or 6 wherein the separation element comprises an inert support.

10. The method of any one of claims 1, 5, or 6 wherein the separation element comprises an inert solid support.

11. The method of any one of claims 1, 5, or 6 wherein said extending step comprises using four different nucleotides selected from the group consisting of dATP, dCTP, dGTP, dTTP, dUTP, dITP, ddATP, ddCTP, ddGTP, ddITP, and ddTTP, and wherein said nucleotides incorporate at least one element selected from the group consisting of a detectable element and a separation element.

12. The method of claim 11 wherein at least one of said nucleotides includes a detectable element.

13. The method of claim 11 wherein at least one of said nucleotides includes a separation element.

14. The method of claim 11 wherein at least one of said nucleotides includes separation and detectable elements.

15. The method of any one of claims 1, 5, or 6 wherein said extending step comprises using one nucleotide sequence selected from the group consisting of ddITP, ddATP, ddCTP, ddGTP, and ddTTP, and wherein said nucleotide incorporates at least one element selected from the group consisting of a detectable element and a separation element.

16. The method of claim 15 wherein said nucleotide includes a detectable element.

17. The method of claim 15 wherein said nucleotide includes a separation element.

18. The method of claim 15 wherein said nucleotide includes separation and detectable elements.

19. The method of any one of claims 1, 5, or 6 wherein said separating step comprises, contacting any extended primer with a molecule having affinity for said separation element; and separating said contacted extended primer(s) to provide said fraction wherein said separation element and said molecule are selected from the group listed as follows;

| Separation Element | Molecule Having Affinity for Separation Element |
|---|---|
| (a) a ligand for which there is a receptor; | a receptor for the ligand; |
| a receptor; | the ligand for the receptor; |
| (c) an antigen; | an antibody for the antigen; |
| (d) an antibody for an antigen; | the antigen; |
| (e) an antiidiotypic antibody; | an antibody for the antiidiotypic antibody; |
| (f) an antibody for an antiidiotypic antibody; | an antiidiotypic antibody for the antibody; |
| (i) a haptenic group; | an antibody for the haptenic group; |
| (h) an antibody for a haptenic group; | the haptenic group; |
| (i) an enzyme; | a binding inhibitor for the enzyme; and |
| (j) a binding inhibitor for an enzyme; | the enzyme. |

20. The method of any one of claims 1, 5, or 6 wherein the specific polynucleotide sequence(s) is a DNA sequence.

21. The method of any one of claims 1, 5, or 6 wherein the specific polynucleotide sequence(s) is an RNA sequence.

22. The method of any one of claims 1, 5, or 6 wherein the specific polynucleotide sequence(s) is from an organism selected from the of infectious organisms and disease causing organisms.

23. The method of any one of claims 1, 5, or 6 wherein the oligonucleotide primer incorporates a detectable element at its 5' end.

24. The method of any one of claims 1, 5, or 6 wherein the separating step is a washing step.

25. The method of claim 5 or claim 6 wherein each of said primers incorporates a different separation element.

26. The method of claim 5 or claim 6 wherein said separating step comprises: contacting any extended primers with molecules having affinity for the separation elements, said molecules being linked to supports that facilitate said separating; and separating said contacted extended primers to provide said fraction.

27. The method of claim 26 wherein said separation elements and said molecules are selected from the group listed as follows:

| Separation Element | Molecule Having Affinity for Separation Element |
| --- | --- |
| (a) a ligand for which there is a specific receptor; | a specific receptor for the ligand; |
| (b) a specific receptor; | the ligand for the specific receptor; |
| (c) an antigen; | a specific antibody of the antigen; |
| (d) a specific antibody for antigen; | the antigen; |

-continued

| Separation Element | Molecule Having Affinity for Separation Element |
| --- | --- |
| (e) an antiidiotypic antibody; | a specific antibody of the antiidiotypic antibody; |
| (f) an antibody for an antiidiotypic antibody; | an antiidiotypic antibody specific for the antibody; |
| (g) a haptenic group; | a specific antibody of the haptenic group; |
| (h) a specific antibody for a haptenic group; | the haptenic group; |
| (i) an enzyme; | a tight binding inhibitor for the enzyme; and |
| (j) a tight binding inhibitor for an enzyme; | the enzyme. |

28. The method of claim 26 wherein said supports are test strips.

29. The method of claim 28 wherein said separating step comprises precipitating any extended primer(s) and resuspending said extended primer(s) in a solution conducive to binding of said separation element(s) to a molecule(s) having affinity for said separation element(s).

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:1:

TGACCGGCAG CAAAATG      17

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i v ) ANTI-SENSE: YES ( x i ) SEQUENCE DESCRIPTION: SEQ ID NO:2:

TTTGCTGCCG GTCACGGTTC GAA      23

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AAACGACGGC CAGTGCC      17

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACGTTGTAA AACGACGGCC AGTGCC      25

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TTTCCTGGAT TATGCCTGGC AC      22

( 2 ) INFORMATION FOR SEQ ID NO:6:

( i ) SEQUENCE CHARACTERISTICS:

( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

GTATCTATAT TCATCATAGG AAACAC 26

( 2 ) INFORMATION FOR SEQ ID NO:7:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:7:

TTTCCTGGAT TATGCCTGGC ACCATTAAAG AAAATATCAT 40

( 2 ) INFORMATION FOR SEQ ID NO:8:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:8:

TTTCCTGGAT TATGCCTGGC ACCATTAAAG AAAATATCAT CTTGGTGTT TCCTATGATG 60

AATATAGATA C 71

( 2 ) INFORMATION FOR SEQ ID NO:9:

( i ) SEQUENCE CHARACTERISTICS:
( A ) LENGTH: 71 base pairs
( B ) TYPE: nucleic acid
( C ) STRANDEDNESS: single
( D ) TOPOLOGY: linear ( i i ) MOLECULE TYPE: DNA (genomic)

( i v ) ANTI-SENSE: YES ( x i ) SEQUENCE DESCRIPTION: SEQ ID NO:9:

AAAGGACCTA ATACGGACCG TGGTAATTTC TTTTATAGTA GAAACCACAA AGGATACTAC 60

TTATATCTAT G 71

( 2 ) INFORMATION FOR SEQ ID NO:10:

( i ) SEQUENCE CHARACTERISTICS:
( A ) LENGTH: 68 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:10:

TTTCCTGGAT TATGCCTGGC ACCATTAAAG AAAATATCAT TGGTGTTTCC TATGATGAAT 60

ATAGATAC 68

```
(2) INFORMATION FOR SEQ ID NO:11:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (xi) SEQUENCE DESCRIPTION: SEQ ID NO:11:

AAAGGACCTA ATACGGACCG TGGTAATTTC TTTTATAGTA ACCACAAAGG ATACTACTTA          60

TATCTATG                                                                  68
```